United States Patent
Tamura

(10) Patent No.: US 10,524,745 B2
(45) Date of Patent: Jan. 7, 2020

(54) DATA ACQUISITION DEVICE, X-RAY CT APPARATUS, AND NUCLEAR MEDICINE DIAGNOSTIC APPARATUS

(71) Applicant: Toshiba Medical Systems Corporation, Otawara-shi (JP)

(72) Inventor: Emi Tamura, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 521 days.

(21) Appl. No.: 15/339,156

(22) Filed: Oct. 31, 2016

(65) Prior Publication Data
US 2017/0119325 A1    May 4, 2017

(30) Foreign Application Priority Data

Nov. 2, 2015  (JP) .................................. 2015-216159
Oct. 28, 2016  (JP) .................................. 2016-211542

(51) Int. Cl.
*A61B 6/00* (2006.01)
*A61B 6/03* (2006.01)

(52) U.S. Cl.
CPC ............ *A61B 6/4241* (2013.01); *A61B 6/032* (2013.01)

(58) Field of Classification Search
None
See application file for complete search history.

(56) References Cited

U.S. PATENT DOCUMENTS

| 7,646,845 | B2 | 1/2010 | Lecomte et al. |
| 2012/0184848 | A1* | 7/2012 | Ohi ..................... G01T 1/1647 600/436 |
| 2014/0185760 | A1* | 7/2014 | Kim .................... A61B 6/4241 378/62 |
| 2014/0270055 | A1 | 9/2014 | Oikawa et al. |
| 2015/0327827 | A1 | 11/2015 | Teshigawara |
| 2016/0081637 | A1 | 3/2016 | Noshi et al. |
| 2016/0095560 | A1 | 4/2016 | Nakai |

FOREIGN PATENT DOCUMENTS

| JP | 2014/64756 | 4/2014 |
| JP | 2014-176620 | 9/2014 |
| JP | 2015-13107 | 1/2015 |
| JP | 2015-24128 | 2/2015 |

* cited by examiner

*Primary Examiner* — Hoon K Song
(74) *Attorney, Agent, or Firm* — Oblon, McClelland, Maier & Neustadt, L.L.P.

(57) ABSTRACT

A data acquisition device according to an embodiment includes processing circuitry. The processing circuitry is configured to compare the reference waveform of a signal, which is output from a detector that detects radiation, with the waveform of a detection signal based on the radiation, which enters the detector through the subject and which is detected by the detector. The processing circuitry is configured to estimate the information about the radiation, which enters the detector through the subject, in accordance with a comparison result.

13 Claims, 16 Drawing Sheets

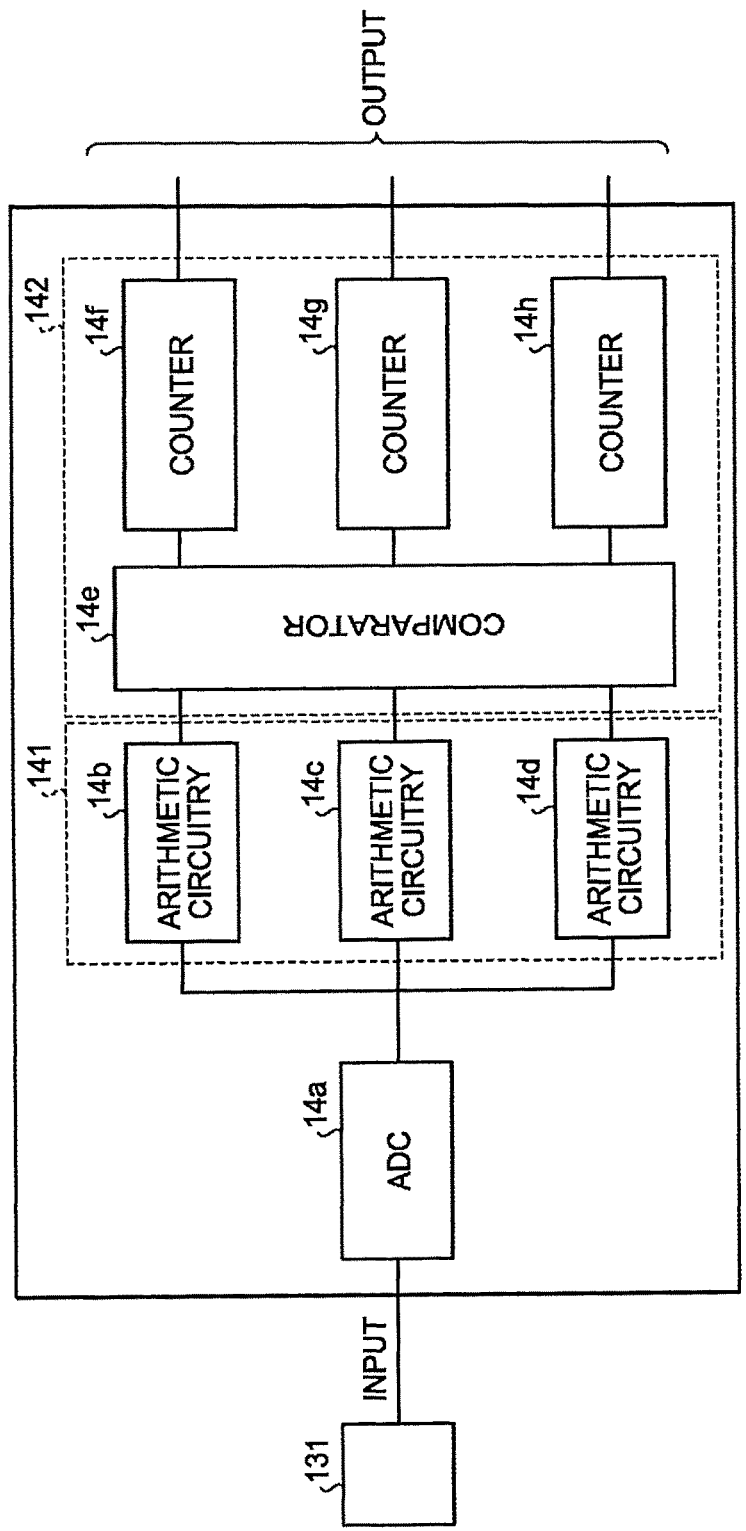

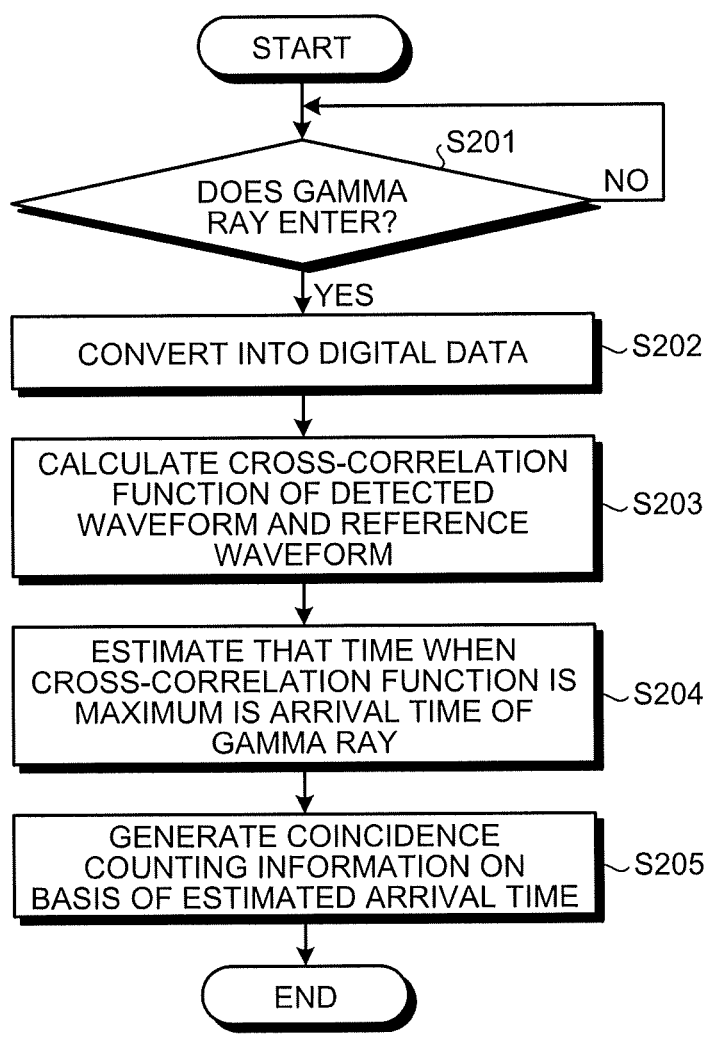

US 10,524,745 B2

DATA ACQUISITION DEVICE, X-RAY CT APPARATUS, AND NUCLEAR MEDICINE DIAGNOSTIC APPARATUS

CROSS-REFERENCE TO RELATED APPLICATIONS

This application is based upon and claims the benefit of priority from Japanese Patent Application No. 2015-216159, filed on Nov. 2, 2015; and Japanese Patent Application No. 2016-211542, filed on Oct. 28, 2016, the entire contents of which are incorporated herein by reference.

FIELD

Embodiments described herein relate generally to a data acquisition device, an X-ray CT apparatus, and a nuclear medicine diagnostic apparatus.

BACKGROUND

Conventionally, in medical image systems, such as photon-counting type X-ray computed tomography (CT) apparatus, or positron emission tomography (PET) apparatus, photon-counting type detectors are used, and photon counting is conducted on X-rays, transmitted through the subject, or gamma rays based on an isotope or labeled compound, selectively incorporated in living tissues of the subject.

For example, for photon-counting CT, direct-conversion type semiconductor detectors of cadmium telluride (CdTe), cadmium Zinc telluride (CdZnTe), or the like, or indirect-conversion type detectors of a scintillator, or the like, are used as a detector. Furthermore, for photon-counting CT, for example, an integrated circuit, such as an application specific integrated circuit (ASIC), is provided near the detector so that signals, output from the detector, are processed to acquire data.

For example, the ASIC, used for photon-counting CT, amplifies an output signal from the detector by using an amplifier, shapes its waveform, and then counts the number of incident X-ray photons of each of the windows, which are divided in accordance with the level of the signal. Here, during the photon-counting CT, the counter repeats output (or memory storage) and reset at a constant interval (view) so as to acquire the data on one cycle, thereby acquiring CT images in multiple energy windows.

BRIEF DESCRIPTION OF THE DRAWINGS

FIG. 4 is a diagram that illustrates an example of the configuration of data acquisition circuitry according to the first embodiment;
FIG. 14 is a flowchart that illustrates the steps of the operation performed by the PET apparatus according to the second embodiment.

DETAILED DESCRIPTION

According to an embodiment, a data acquisition device includes processing circuitry. The processing circuitry is configured to compare the reference waveform of a signal, which is output from a detector that detects radiation, with the waveform of a detection signal based on the radiation, which enters the detector through the subject and which is detected by the detector. The processing circuitry is configured to estimate the information about the radiation, which enters the detector through the subject, in accordance with a comparison result.

With reference to the attached drawings, a detailed explanation is given below of an embodiment of a data acquisition device, an X-ray CT apparatus, and a nuclear medicine diagnostic apparatus. Furthermore, in the following embodiment, an explanation is given by using, for example, a photon-counting type X-ray CT apparatus as the X-ray CT apparatus and a PET apparatus as the nuclear medicine diagnostic apparatus.

First Embodiment

Figure 1:
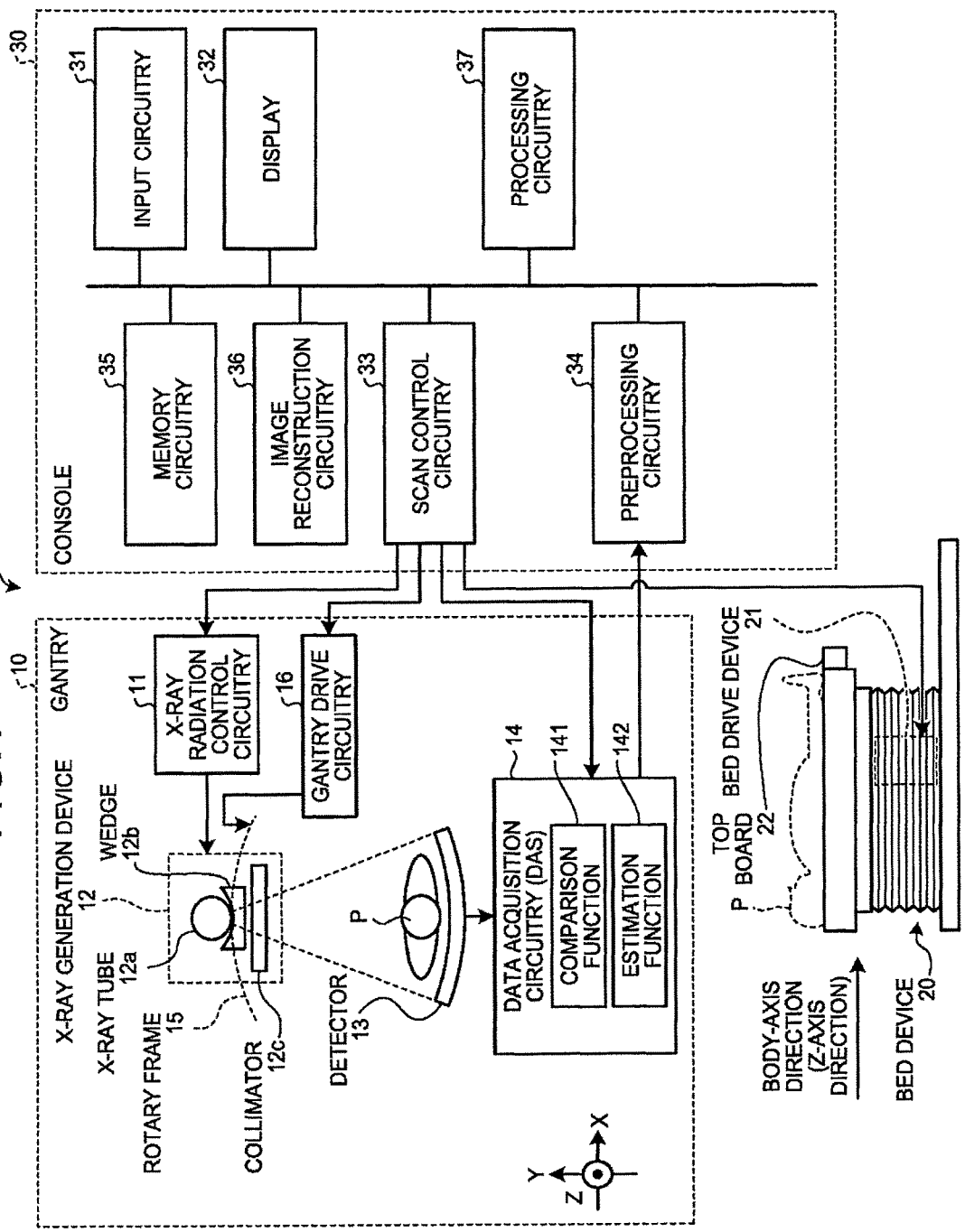
FIG. 1 is a diagram that illustrates an example of the configuration of a photon-counting type X-ray CT apparatus according to a first embodiment.

First, an explanation is given of an embodiment of the photon-counting type X-ray CT apparatus. FIG. 1 is a diagram that illustrates an example of the configuration of a photon-counting type X-ray CT apparatus 1 according to a first embodiment. As illustrated in FIG. 1, the photon-counting type X-ray CT apparatus 1 according to the first embodiment includes a gantry 10, a bed device 20, and a console 30.

The gantry 10 is a device that emits X-rays to a subject P (patient), detects the X-rays that are transmitted through the subject P, and outputs them to the console 30, and it includes X-ray radiation control circuitry 11, an X-ray generation device 12, a detector 13, data acquisition circuitry (DAS: Data Acquisition System) 14, a rotary frame 15, and gantry drive circuitry 16.

The rotary frame 15 is an annular frame that supports the X-ray generation device 12 and the detector 13 such that they are opposed to each other with the subject P interposed therebetween and that is rotated at high speed in a circular orbit around the subject P by the gantry drive circuitry 16 that is described later.

The X-ray radiation control circuitry 11 is a device that serves as a high-voltage generation unit and that supplies a high voltage to an X-ray tube 12a, and the X-ray tube 12a generates X-rays by using the high voltage that is supplied from the X-ray radiation control circuitry 11. Under the control of scan control circuitry 33, which is described later, the X-ray radiation control circuitry 11 adjusts the tube voltage or the tube current that is supplied to the X-ray tube 12a, thereby adjusting the amount of X-rays that are emitted to the subject P.

Furthermore, the X-ray radiation control circuitry 11 switches a wedge 12b. Furthermore, the X-ray radiation control circuitry 11 adjusts the numerical aperture of a collimator 12c, thereby adjusting the radiation range (the fan angle or the cone angle) of X-rays. Moreover, according to the present embodiment, there may be a case where multiple types of wedges are manually switched by an operator.

The X-ray generation device 12 is a device that generates X-rays and emits the generated X-rays to the subject P, and it includes the X-ray tube 12a, the wedge 12b, and the collimator 12c.

The X-ray tube 12a is a vacuum tube that emits X-ray beams to the subject P by using the high voltage that is supplied by the X-ray radiation control circuitry 11, and it emits X-ray beams to the subject P in accordance with the rotation of the rotary frame 15. The X-ray tube 12a generates X-ray beams that spread with the fan angle and the cone angle. For example, under the control of the X-ray radiation control circuitry 11, the X-ray tube 12a is capable of continuously emitting X-rays all around the subject P for a full reconstruction or continuously emitting X-rays for a half reconstruction within an emission range (180°+the fan angle) that enables a half reconstruction. Furthermore, under the control of the X-ray radiation control circuitry 11, the X-ray tube 12a is capable of intermittently emitting X-rays (pulse X-rays) at a previously set position (tube position). Furthermore, the X-ray radiation control circuitry 11 is capable of changing the intensity of X-rays, emitted from the X-ray tube 12a. For example, the X-ray radiation control circuitry 11 increases the intensity of X-rays, emitted from the X-ray tube 12a, at a specific tube position, and it decreases the intensity of X-rays, emitted from the X-ray tube 12a, in the area other than the specific tube position.

The wedge 12b is an X-ray filter that adjusts the amount of X-rays with regard to the X-rays that are emitted from the X-ray tube 12a. Specifically, the wedge 12b is a filter that transmits and attenuates X-rays, emitted from the X-ray tube 12a, such that X-rays, emitted from the X-ray tube 12a to the subject P, has a predetermined distribution. For example, the wedge 12b is a filter that is obtained by processing aluminum so as to have a predetermined target angle or a predetermined thickness. Furthermore, the wedge is also called a wedge filter or a bow-tie filter.

The collimator 12c is a slit that narrows the irradiation range of X-rays, of which the amount of X-rays has been adjusted by the wedge 12b, under the control of the X-ray radiation control circuitry 11 that is described later.

The gantry drive circuitry 16 drives and rotates the rotary frame 15 so that the X-ray generation device 12 and the detector 13 are rotated in a circular orbit around the subject P.

Each time an X-ray photon enters, the detector 13 outputs the signal with which the energy value of the X-ray photon may be measured. The X-ray photon is, for example, an X-ray photon that is emitted from the X-ray tube 12a and is transmitted through the subject P. The detector 13 includes multiple detection elements that output an electric signal (analog signal) of 1 pulse each time an X-ray photon enters. The photon-counting type X-ray CT apparatus 1 counts the number of electric signals (pulses) so as to count the number of X-ray photons that enter each of the detection elements. Furthermore, the photon-counting type X-ray CT apparatus 1 performs arithmetic processing on the signal so as to measure the energy value of the X-ray photon that causes output of the signal.

The above-described detection element includes, for example, a scintillator and an optical sensor, such as a photomultiplier tube. In such a case, the detector 13, illustrated in FIG. 1, is an indirect-conversion type detector that converts the incident X-ray photon into scintillator light by using the scintillator and converts the scintillator light into an electric signal by using the optical sensor, such as a photomultiplier tube. Furthermore, there may be a case where the above-described detection element is a semiconductor device of, for example, cadmium telluride (CdTe), cadmium zinc telluride (CdZnTe), or the like. In such a case, the detector 13, illustrated in FIG. 1, is a direct-conversion type detector that directly converts the incident X-ray photon into an electric signal.

For example, the detector 13, illustrated in FIG. 1, is a plane detector in which detection elements are arranged in N columns in the channel direction (the direction of the X axis in FIG. 1) and in M columns in the direction of the rotational center axis of the rotary frame 15 (the direction of the Z axis in FIG. 1) where the gantry 10 is not tilted. When a photon enters, the detection element outputs an electric signal of 1 pulse. The photon-counting type X-ray CT apparatus 1 discriminates among individual pulses that are output from a detection element 131, thereby counting the number of X-ray photons that enter the detection element 131. Furthermore, the photon-counting type X-ray CT apparatus 1 performs arithmetic processing based on the intensity of a pulse, thereby measuring the energy value of the counted X-ray photon.

The data acquisition circuitry 14 is a DAS, and it acquires the detection data on X-rays that are detected by the detector 13. For example, the data acquisition circuitry 14 generates the count data that is obtained by counting the photons (X-ray photons), which come from the X-ray that is transmitted through the subject, for each energy band, and it transmits the generated count data to the console 30 that is described later. For example, if X-rays are continuously emitted from the X-ray tube 12a while the rotary frame 15 is rotated, the data acquisition circuitry 14 acquires the group of count data for the entire periphery (360 degrees). Furthermore, the data acquisition circuitry 14 transmits each acquired count data in relation to the tube position to the console 30 that is described later. The tube position is the information that indicates the projection direction of the count data. Moreover, as illustrated in FIG. 1, the data acquisition circuitry 14 performs a comparison function 141 and an estimation function 142, which are explained in detail later.

The bed device 20 is a device on which the subject P is placed and, as illustrated in FIG. 1, it includes a bed drive device 21 and a top board 22. The bed drive device 21 moves the top board 22 in the direction of the Z axis to move the subject P into the rotary frame 15. The top board 22 is a board on which the subject P is placed. Furthermore, in the present embodiment, an explanation is given of a case where the relative position between the gantry 10 and the top board 22 is changed by controlling the top board 22; however, this is not a limitation on the embodiment. For example, if the gantry 10 is self-propelling, the relative position between the gantry 10 and the top board 22 may be changed by controlling driving of the gantry 10.

Furthermore, for example, the gantry 10 conducts helical scan to scan the subject P in a helical fashion by rotating the rotary frame 15 while the top board 22 is moved. Alternatively, the gantry 10 conducts conventional scan to scan the subject P in a circular orbit by rotating the rotary frame 15 with the position of the subject P fixed after the top board 22 is moved. Alternatively, the gantry 10 implements a step-and-shoot method to conduct conventional scan at multiple scan areas by moving the position of the top board 22 at a constant interval.

The console 30 is a device that receives an operation of the photon-counting type X-ray CT apparatus 1 from an operator and that reconstructs X-ray CT image data by using the projection data that is acquired by the gantry 10. As illustrated in FIG. 1, the console 30 includes input circuitry 31, a display 32, the scan control circuitry 33, preprocessing circuitry 34, memory circuitry 35, image reconstruction circuitry 36, and processing circuitry 37.

The input circuitry 31 includes a mouse, keyboard, trackball, switch, button, joystick, or the like, which is used by an operator of the photon-counting type X-ray CT apparatus 1 to input various commands or various settings, and it transfers the information on the command or setting, received from the operator, to the processing circuitry 37. For example, the input circuitry 31 receives, from an operator, a capturing condition for X-ray CT image data, a reconstruction condition for reconstructing X-ray CT image data, an image processing condition for X-ray CT image data, or the like.

The display 32 is a monitor that is viewed by an operator and, under the control of the processing circuitry 37, it displays the image data, generated from X-ray CT image data, to the operator or displays a graphical user interface (GUI) for receiving various commands, various settings, or the like, from the operator via the input circuitry 31.

The scan control circuitry 33 controls operations of the X-ray radiation control circuitry 11, the gantry drive circuitry 16, the data acquisition circuitry 14, and the bed drive device 21 under the control of the processing circuitry 37, thereby controlling data acquisition processing by the gantry 10.

The preprocessing circuitry 34 performs correction processing, such as logarithmic conversion processing, offset correction, sensitivity correction, or beam hardening correction, on the count data that is generated by the data acquisition circuitry 14, thereby generating corrected projection data.

The memory circuitry 35 stores the projection data that is generated by the preprocessing circuitry 34. Furthermore, the memory circuitry 35 stores the image data, or the like, which is generated by the image reconstruction circuitry 36 that is described later. Moreover, the memory circuitry 35 appropriately stores processing results of the processing circuitry 37 that is described later.

The image reconstruction circuitry 36 reconstructs X-ray CT image data by using the projection data that is stored in the memory circuitry 35. Here, the reconstruction method includes various methods, and it may be, for example, back projection processing. Furthermore, the back projection processing may include, for example, back projection processing by using a filtered back projection (FBP) method. Alternatively, the image reconstruction circuitry 36 may also use a successive approximation technique to reconstruct X-ray CT image data. Furthermore, the image reconstruction circuitry 36 conducts various types of image processing on X-ray CT image data, thereby generating image data. Then, the image reconstruction circuitry 36 stores, in the memory circuitry 35, the reconstructed X-ray CT image data or the image data that is generated during various types of image processing.

The processing circuitry 37 controls operations of the gantry 10, the bed device 20, and the console 30 so as to perform the overall control on the photon-counting type X-ray CT apparatus 1. Specifically, the processing circuitry 37 controls the scan control circuitry 33 so as to control CT scan that is conducted by the gantry 10. Furthermore, the processing circuitry 37 controls the image reconstruction circuitry 36 so as to control image reconstruction processing or image generation processing by the console 30. Furthermore, the processing circuitry 37 performs control such that various types of image data, stored in the memory circuitry 35, are displayed on the display 32.

Heretofore, the overall configuration of the photon-counting type X-ray CT apparatus 1 according to the first embodiment is explained. Here, each processing function, performed by each of the above-described circuitry, is stored in the memory circuitry 35 in the form of the program that is executable by the computer. Furthermore, each circuitry reads and executes each program from the memory circuitry 35, thereby performing the above-described various functions. For example, the comparison function 141 and the estimation function 142, which are components of the data acquisition circuitry 14, are stored in the memory circuitry 35 in the form of a program that is executable by the computer. The data acquisition circuitry 14 is a processor that reads and executes each program from the memory circuitry 35 to implement the function that corresponds to each program. In other words, the data acquisition circuitry 14 has each of the functions, illustrated in FIG. 1, after each of the programs has been read. Moreover, the data acquisition circuitry 14, explained in the present embodiment, is equivalent to processing circuitry that is described in a claim.

Furthermore, the word "processor", used in the above explanations, means for example a central processing unit (CPU), a graphics processing unit (GPU), or a circuit, such as an application specific integrated circuit (ASIC), or a programmable logic device (e.g., a simple programmable logic device: SPLD, a complex programmable logic device: CPLD, or a field programmable gate array: FPGA). The processor reads and executes the program, stored in the memory circuitry, to perform the function. Furthermore, a configuration may be such that, instead of storing a program in the memory circuitry, a program is directly installed in a circuit of the processor. In this case, the processor reads and executes the program, installed in the circuit, to perform the function. Furthermore, with regard to the processors according to the present embodiment, instead of the case where each processor is configured as a single circuit, multiple independent circuits may be combined to be configured as a single processor to implement the function.

With the above-described configuration, the photon-counting type X-ray CT apparatus 1 according to the first embodiment allows an improvement in the image quality due to an operation of the data acquisition circuitry 14, which is described in detail below. Specifically, the data acquisition circuitry 14 uses the reference waveform of the signal, output from the detector 13, to estimate the energy of X-rays that are transmitted through the subject, whereby the effect of pile-up is reduced even at high dose, and the image quality is improved.

Figure 2:
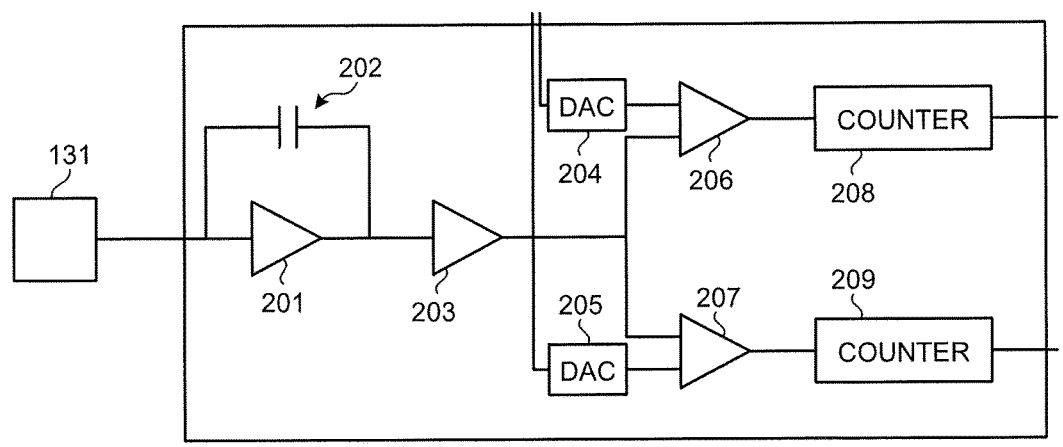
FIG. 2 is a diagram that illustrates an example of detection circuit that is included in the photon-counting type X-ray CT apparatus according to a conventional technology.

Here, an explanation is first given of a case where the image quality is deteriorated in a conventional photon-counting type X-ray CT apparatus. FIG. 2 is a diagram that illustrates an example of the detection circuit that is included in the photon-counting type X-ray CT apparatus according to a conventional technology. For example, in the conventional photon-counting type X-ray CT apparatus, the detection circuit, illustrated in FIG. 2, is provided near the detector, and it discriminates among signals, output from the detection element 131, and counts them. For example, as illustrated in FIG. 2, the conventional detection circuit includes a pre-amplifier 201, a capacitor 202, a shaper 203, digital-to-analog converters (DACs) 204 and 205, comparators 206 and 207, and counters 208 and 209.

Furthermore, after the detection element 131 outputs a signal (charge pulse), the pre-amplifier 201 and the capacitor 202 convert the pulse, generated due to the electric charge, into a voltage, and outputs the voltage pulse. Then, the shaper 203 shapes the waveform of the voltage pulse and outputs it to the comparators 206 and 207. Here, the comparators 206 and 207 compare the input voltage pulse with the threshold, converted into an analog signal by the DACs 204 and 205, and, if the value of the voltage pulse exceeds the threshold, outputs the electric signal to the counter at the subsequent stage. The counters 208 and 209 count the electric signals that are output from the comparators 206 and 207, respectively.

Figure 3A:
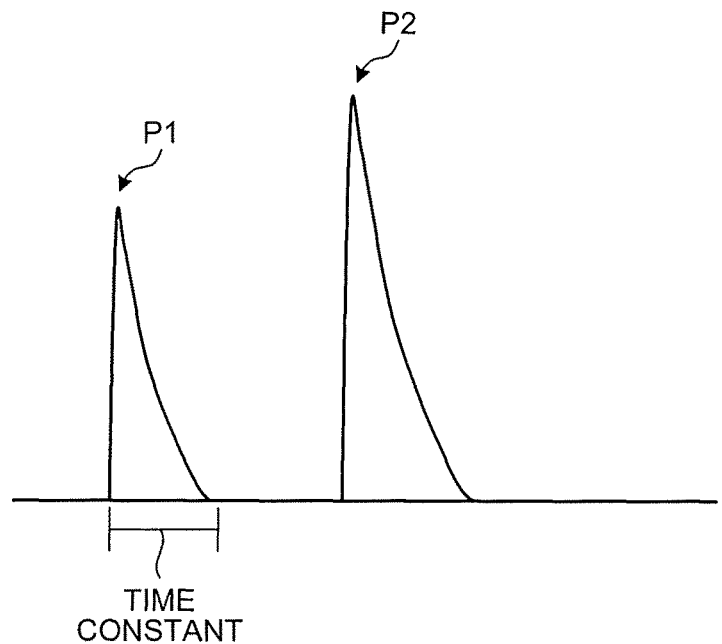
FIG. 3A is a diagram that illustrates the problem of the conventional technology.
Figure 3B:
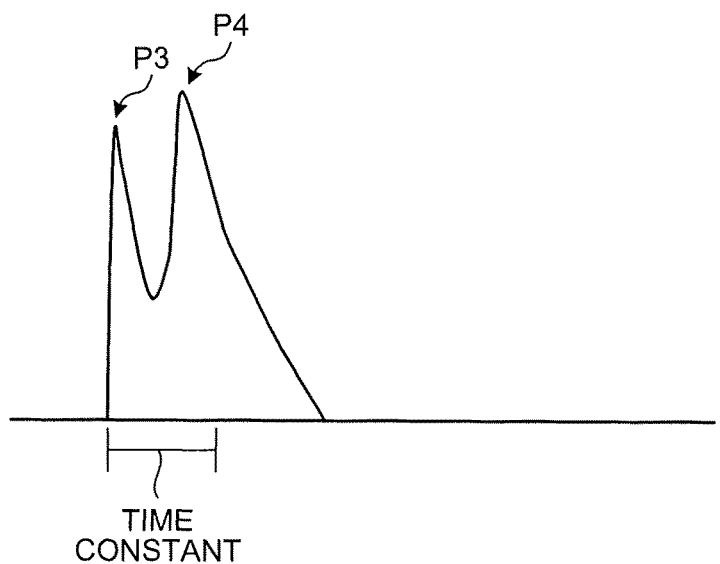
FIG. 3B is a diagram that illustrates the problem of the conventional technology.

Here, the threshold, input from the DAC, is set to any value so that X-ray photons may be counted for each desired energy band. As described above, in the conventional photon-counting type X-ray CT apparatus, the count data is acquired by the detection circuit that is illustrated in FIG. 2; however, if the X-ray with a high intensity enters the detection element 131 (at high dose), there is a case where it is difficult to discriminate among individual pulses and the image quality is deteriorated. FIGS. 3A and 3B are diagrams that illustrate the problem of the conventional technology. Here, FIG. 3A illustrates the pulses that are output if the X-ray with a low intensity enters the detection element 131. Furthermore, FIG. 3B illustrates the pulses that are output if the X-ray with a high intensity enters the detection element 131.

For example, if the intensity of the X-ray is low, the incidence interval of the incident photons is large; therefore, as illustrated in FIG. 3A, it is possible to discriminate between two pulses P1 and P2, which come from the two photons that enter the same detection element. Here, in the photon-counting type X-ray CT apparatus, as illustrated in FIG. 3A, the time constant ($\tau$) is defined based on the detector and the electric circuit, and the responsiveness for signals is determined by the time constant. For example, if the time constant is 100 ns ($=1 \times 10^{-7}$ s), it is theoretically difficult to count incident photons that exceed $10^7$/s.

The X-ray photons, counted by the photon-counting type X-ray CT apparatus, do not enter at a constant interval but they enter at random; therefore, if the intensity of the X-ray is high, photons enter at an interval that is shorter than the time constant. In such a case, for example, as illustrated in FIG. 3B, a second pulse P4 is piled up on a first pulse P3 and thus they are apparently determined as a single pulse. That is, the pulse P3 and the pulse P4 are not discriminated and they are counted as the single pulse P3 by the counter 208 or the counter 209. As a result, in the conventional photon-counting type X-ray CT apparatus, data is missing or the value of the voltage pulse is wrong, which results in a degradation in the image quality of the generated image.

Here, the current photon-counting type X-ray CT apparatus principally use a direct-conversion type detector, which uses a semiconductor as the detector. Because of a short time constant and a high response speed, the direct-conversion type detector is unlikely to be affected by the above-described pile-up even at high dose. However, in the case of the direct-conversion type detector, the absorption efficiency of X-rays is often low, and the stability is low. Furthermore, the costs of the direct-conversion type detector are also high. Therefore, there is an expectation for application of the indirect-conversion type detector, which has a high absorption efficiency of X-rays and a high stability, to the photon-counting type X-ray CT apparatus. Thus, according to the present embodiment, the photon-counting type X-ray CT apparatus with a higher stability is provided, in which the effect of pile-up is reduced due to an operation of the data acquisition circuitry 14 so that the image quality is improved, and to which an indirect-conversion type detector is applied.

Specifically, the data acquisition circuitry 14 according to the first embodiment performs the comparison function 141 and the estimation function 142, whereby the image quality is improved. The comparison function 141 compares the reference waveform of the signal, output from the detector 13 that detects radiation, with the waveform of the detection signal based on the radiation, which enters the detector through the subject and which is detected by the detector 13. Specifically, the comparison function 141 compares the waveform of the detection signal based on the X-ray, which is transmitted through the subject and enters the detector 13, with the reference waveform of each X-ray energy in the detector 13. For example, the comparison function 141 extracts a predetermined area, including the peak of the waveform of the detection signal, and compares the waveform of the extracted predetermined area with the waveform of the area, which corresponds to the predetermined area, included in the reference waveform of each X-ray energy. Specifically, the reference waveform of the signal, output from the detector 13, is previously stored, and the comparison function 141 compares the waveform of the detection signal, detected by the detector 13, with the reference waveform.

Here, the data acquisition circuitry 14 performs the following operation to compensate for the effect of pile-up. Specifically, the comparison function 141 divides multiple peaks, included in the waveform of the detection signal, as each detection signal that is caused by the incidence of a single photon, uses the waveform that corresponds to the previous peak among the peaks to correct the subsequent peak, and compares the waveform of the predetermined area, including the previous peak, and the waveform of the predetermined area, including the corrected subsequent peak, with the reference waveform of each X-ray energy. Here, the comparison function 141 determines that the reference waveform, which approximates the waveform of the predetermined area that includes the previous peak, is the waveform that corresponds to the previous peak, and it uses the reference waveform, which is determined to be the waveform that corresponds to the previous peak, to correct the height of the subsequent peak.

On the basis of the result of comparison by the comparison function 141, the estimation function 142 estimates the information about the radiation that enters the detector 13 through the subject. Specifically, the estimation function 142 estimates that the energy, which corresponds to the reference waveform that approximates the waveform of the detection signal, is the energy of the X-ray that is transmitted through the subject and that enters the detector 13. For example, the estimation function 142 estimates that the energy, which corresponds to the reference waveform that approximates the waveform in the predetermined area, is the energy of the X-ray that is transmitted through the subject and enters the detector 13.

Here, if pile-up occurs in a detection signal, the estimation function 142 uses each comparison result with regard to the previous peak and the subsequent peak, obtained by the above-described comparison function 141, to estimate the energy of the photon, corresponding to the previous peak, and the energy of the photon, corresponding to the subsequent peak.

An explanation is given below of an example of the configuration for implementing the above-described data acquisition circuitry 14. FIG. 4 is a diagram that illustrates an example of the configuration of the data acquisition circuitry 14 according to the first embodiment. As illustrated in FIG. 4, the data acquisition circuitry 14 according to the first embodiment includes an analog-to-digital converter (ADC) 14a, arithmetic circuitries 14b to 14d, a comparator 14e, and counters 14f to 14h, and it is provided at the subsequent stage of each of the detection elements 131 in the detector 13. Here, in FIG. 4, the arithmetic circuitries 14b to 14d are equivalent to the above-described comparison function 141, and the comparator 14e and the counters 14f to 14h are equivalent to the above-described estimation function 142.

For example, the detection element 131 is formed with the combination of a scintillator, which has a high-speed responsiveness in an available range, and an optical sensor that has an internal amplification function. For example, the scintillator is "Pr:LuAG" with the time constant of "20 ns" or "LSO", "LGSO", or the like, with the time constant of "40 ns", and the optical sensor is "Avalanche PhotoDiode: APD", "silicon photomultiplier: SiPM", or the like.

The ADC 14a converts the pulse signal, output from the detection element 131, into a digital signal. For example, the ADC 14a samples the input pulse signal at a predetermined sampling rate (e.g., 250 megasample per second (Msps)). Then, the ADC 14a outputs the sampling data to each of the arithmetic circuitries 14b to 14d.

The arithmetic circuitries 14b to 14d compare the sampling data, output from the ADC 14a, with the reference waveform of the output signal in the detector 13. Specifically, the arithmetic circuitries 14b to 14d compare the reference sampling data, which is sampled by the ADC 14a from the signal that is obtained when an X-ray is actually emitted to the detector 13, with the sampling data that is sampled by the ADC 14a from the signal that is transmitted through the subject and is then detected. Here, each of the arithmetic circuitries 14b to 14d stores the comparison data that is obtained by modifying the reference sampling data such that it corresponds to the energy band of the X-ray to be discriminated. Then, the arithmetic circuitries 14b to 14d output, to the comparator 14e, the result of comparison between the sampling data, output from the ADC 14a, and the comparison data.

Figure 5:
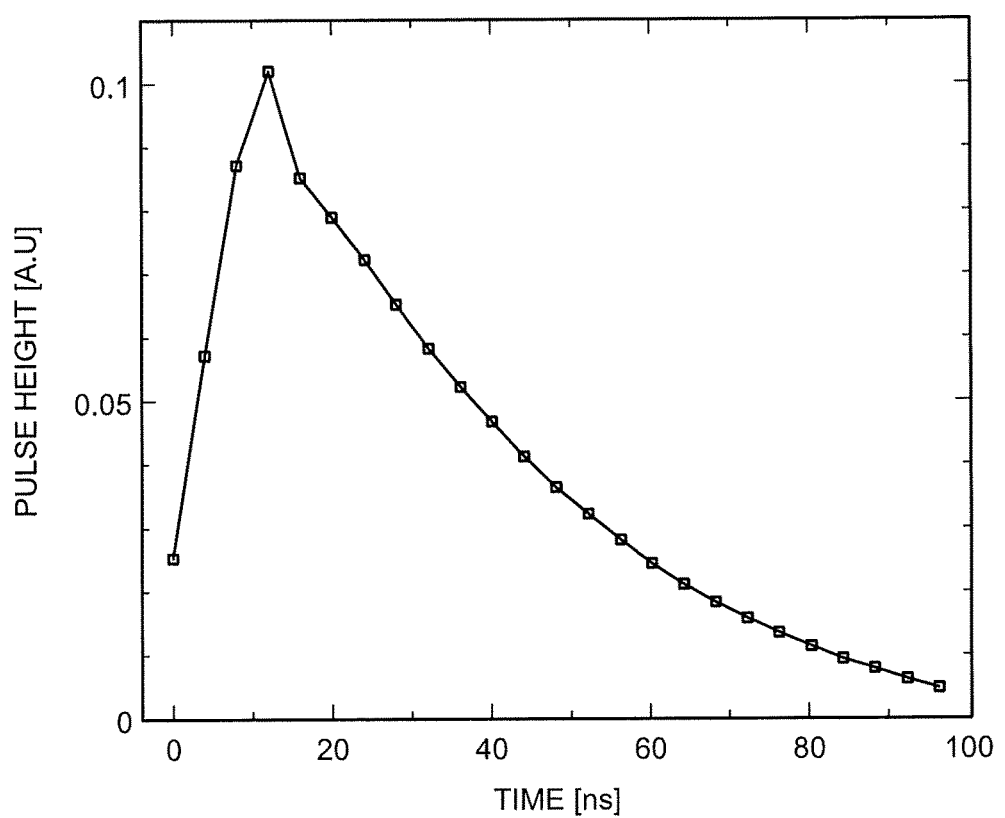
FIG. 5 is a diagram that illustrates an output signal according to the first embodiment.

Here, an explanation is first given of an output signal that is generated due to an individual X-ray photon. FIG. 5 is a diagram that illustrates an output signal according to the first embodiment. FIG. 5 illustrates the average waveform of the output signal that is obtained when the X-ray of 120 keV is emitted to the detector, which has the combination of "scintillator: LGSO" and "optical sensor: SiPM". Furthermore, in FIG. 5, the vertical axis indicates the output value that is normalized by using the integral value in "100 ns". As illustrated in FIG. 5, with regard to the waveform of the signal that is output when the indirect-conversion type detector absorbs a single X-ray photon, the signal sharply rises due to the absorption of the X-ray, and it gradually attenuates with the attenuation time constant of the scintillator. Here, if the X-ray is detected by using the indirect-conversion type detector, the shape of the obtained signal is as illustrated in FIG. 5 regardless of the energy. For example, if the signal, obtained when the X-ray of 60 keV is emitted, is normalized by "100 ns", the same shape as that in FIG. 5 is represented. That is, with regard to the signal of the X-ray, detected by the indirect-conversion type detector, the waveform is substantially the same, and only the height of a pulse is different.

Therefore, according to the present embodiment, the waveform, illustrated in FIG. 5, is used as the reference waveform, and the reference sampling data, acquired from the reference waveform, is compared with the sampling data on the signal based on the X-ray that is transmitted through the subject. Here, as described above, signals of the X-ray, detected by the indirect-conversion type detector, are substantially the same in the waveform and are different in only the height of the pulse; therefore, the reference sampling data is changed such that the height of the reference waveform is changed, whereby it is possible to derive the sampling data that corresponds to various types of energy.

For example, the sampling data on the output waveform, illustrated in FIG. 5, has 25 sample points, and the value of each point is output from the ADC 14a. Here, for example, in the case of the sampling data that corresponds to the energy higher than 120 keV, the value of each point increases while the shape of the waveform is retained. Therefore, by using the relation between the energy of the X-ray and the ups and downs of the pulse, it is possible to acquire the comparison data, corresponding to various types of energy of the X-ray, from the sampling data on the reference waveform. Furthermore, each of the sets of comparison data, corresponding to various types of energy, is compared with the sampling data on the pulse based on the X-ray, transmitted through the subject, and the most approximate comparison data is extracted, whereby the energy of the X-ray, transmitted through the subject, may be estimated.

Here, according to the first embodiment, the comparison data and the sampling data are compared by using the chi-squared test, illustrated in the following Equation (1), so that the energy of the X-ray, transmitted through the subject, is estimated. Here, in Equation (1), "$X^2$" denotes the chi-squared value, "$x_i$" denotes the waveform (output value) based on the X-ray, transmitted through the subject, "template$_i$" denotes the reference waveform, and "$\sigma_i$" denotes data error. Furthermore, "N" in Equation (1) denotes the constant by which the vertical axis of the reference waveform is multiplied.

$$X^2 = \sum_{i=j}^{k} \frac{(x_i - N \times template_i)^2}{\sigma_i^2} \quad (1)$$

Specifically, according to the first embodiment, as represented by Equation (1), the chi-squared test is conducted by using the sampling data and the comparison data in which the height of the reference waveform is changed by using various constants "N", and the energy, corresponding to "N" with the minimum "$X^2$", is estimated as the energy of the X-ray, transmitted through the subject. Here, the relation between the energy of the X-ray and "N" may be previously determined by using the radiation source whose energy is already known. For example, if "$^{57}$Co" is used, the characteristic X-ray, such as "122.1 keV" or "136.5 keV", may be obtained. Then, the waveform of the output signal, obtained when X-rays with various types of energy are emitted to the detector, is compared with the reference waveform, whereby "N", corresponding to each energy, is calculated. Thus, the relation equation of the energy of the X-ray and "N" may be obtained.

Here, one of the methods of estimating the energy of the X-ray by using Equation (1) is that the sampling data based on the X-ray, transmitted through the subject, is applied to Equation (1), "N" with which "$X^2$" is minimum is calculated, and in accordance with the relation equation of the energy of the X-ray and "N", the energy of the X-ray, corresponding to the calculated "N", is calculated. By using this method, it is possible to acquire the detailed information on the energy of the X-ray photon, transmitted through the subject. However, the photon-counting type X-ray CT apparatus 1 may discriminate X-ray photons, transmitted through the subject, for some energy bands. Furthermore, as the photon-counting type X-ray CT apparatus 1 performs processing on each X-ray photon, it is preferable that processing is performed at speed as high as possible.

Therefore, according to the first embodiment, the comparison data "N×template$_i$" is previously calculated with regard to various types of "N", and they are stored in the arithmetic circuitries 14b to 14d, whereby the processing speed is increased. An explanation is given below of an example of a case where, for example, X-ray photons are discriminated in three energy bands of "10 to 20 keV", "20 to 40 keV" and "40 to 50 keV". In such a case, "N", which corresponds to the average value in each energy band, is calculated from the relation equation of the energy of the X-ray and "N", and it is stored in the arithmetic circuitries 14b to 14d. Specifically, each "N", which corresponds to "15 keV", "30 keV", and "45 keV", is calculated, and the comparison data that uses each "N" is stored in the arithmetic circuitries 14b to 14d.

For example, the arithmetic circuitry 14b stores the comparison data "N×template$_i$", which uses "N" that corresponds to "15 keV", calculates the chi-squared value "$X^2$" of the sampling data, output from the ADC 14a, and the comparison data, and outputs it to the comparator 14e. Furthermore, the arithmetic circuitry 14c stores the comparison data "N×template$_i$", which uses "N" that corresponds to "30 keV", calculates the chi-squared value "$X^2$" of the sampling data, output from the ADC 14a, and the comparison data, and outputs it to the comparator 14e.

Moreover, the arithmetic circuitry 14d stores the comparison data "N×template$_i$", which uses "N" that corresponds to "45 keV", calculates the chi-squared value "$X^2$" of the sampling data, output from the ADC 14a, and the comparison data, and outputs it to the comparator 14e.

With reference back to FIG. 4, the comparator 14e compares the three chi-squared values "$X^2$", output from the arithmetic circuitries 14b to 14d, and outputs the electric signal to the counter that corresponds to the energy band of the chi-squared value "$X^2$" that indicates the smallest value. For example, the counters 14f to 14h correspond to "10 to 20 keV", "20 to 40 keV", and "40 to 50 keV", respectively. Here, on the basis of a trigger signal (trigger) that is input from the data acquisition circuitry 14, the counters 14f to 14h conduct counting, outputting of the count value, and resetting of the count value. For example, under the control of the scan control circuitry 33, the data acquisition circuitry 14 outputs a trigger signal during each view, and it controls the counters 14f to 14h so as to output the count data in synchronization with the rotation of the rotary frame 15.

Here, in the case illustrated in FIG. 4, the data acquisition circuitry 14 is provided with the three arithmetic circuitries and the three counters, and it acquires the count data on the three energy bands (energy windows); however, there is no limitation on the embodiment, and there may be a case where two arithmetic circuitries and two counters are provided and the count data on two energy bands is acquired. Furthermore, there may be a case where four or more arithmetic circuitries and counters are provided and the count data on four or more energy bands is acquired.

Figure 6A:
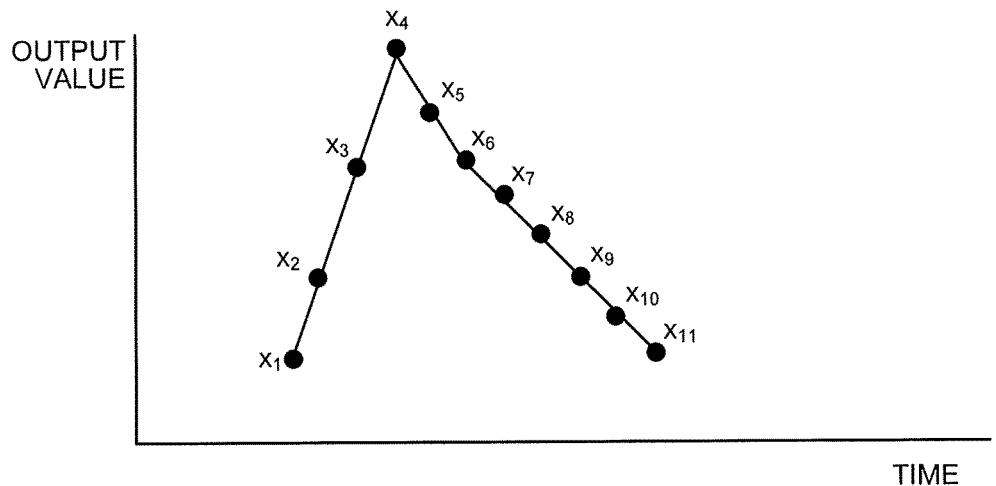
FIG. 6A is a diagram that illustrates an example of an operation of the data acquisition circuitry according to the first embodiment.
Figure 6B:
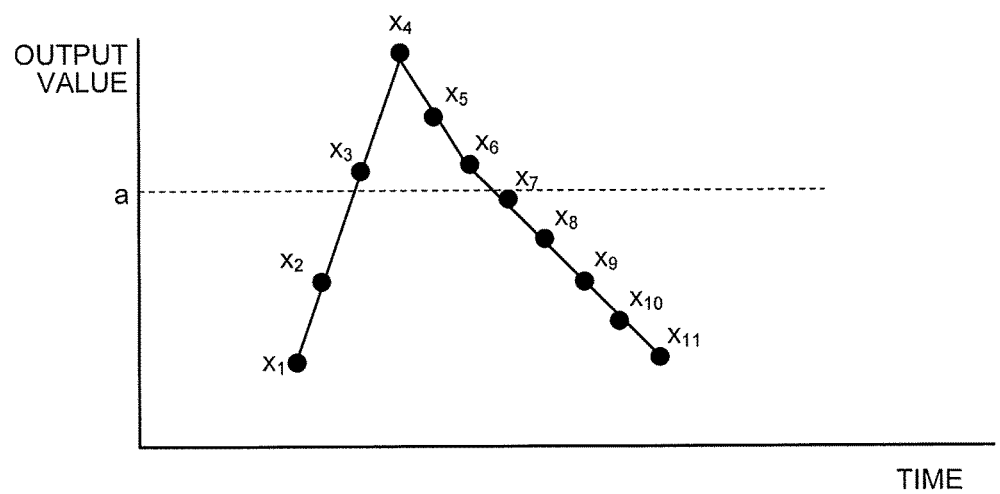
FIG. 6B is a diagram that illustrates an example of an operation of the data acquisition circuitry according to the first embodiment.
Figure 7:
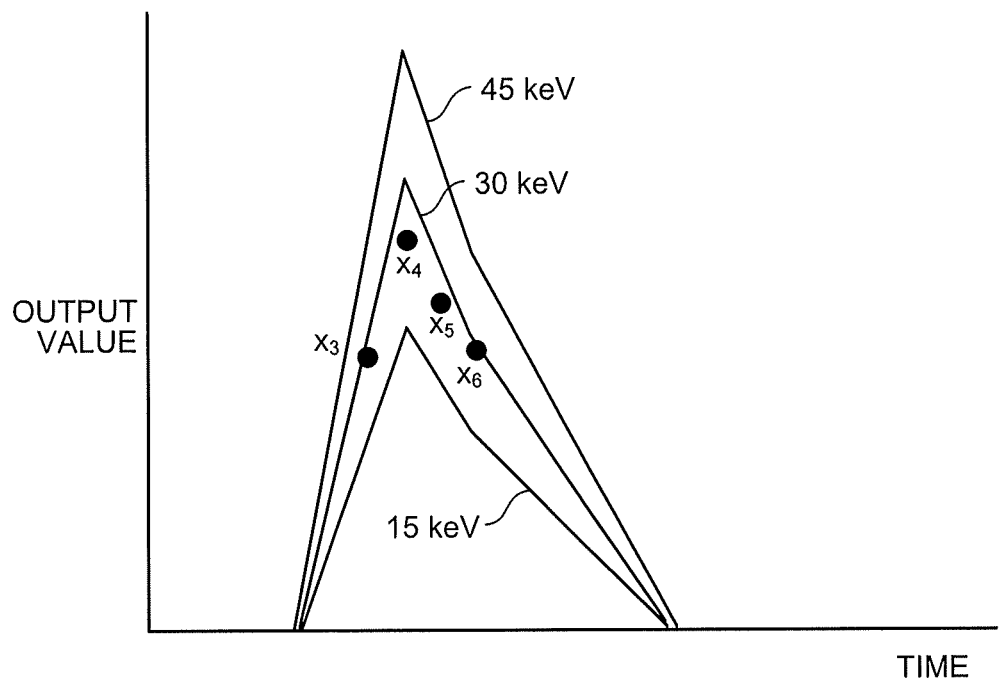
FIG. 7 is a diagram that illustrates an example of an operation of the data acquisition circuitry according to the first embodiment.

An explanation is given below of an example of an operation of the data acquisition circuitry 14 with reference to FIGS. 6A, 6B, and 7. FIGS. 6A, 6B, and 7 are diagrams that illustrate an example of an operation of the data acquisition circuitry 14 according to the first embodiment. For example, in the data acquisition circuitry 14, after the detection element 131 outputs a signal, the ADC 14a conducts sampling on the output signal at a predetermined sampling rate, as illustrated in FIG. 6A. For example, the ADC 14a samples sampling data "$x_1$" to "$x_{11}$" from the output signal, as illustrated in FIG. 6A, and outputs them to the arithmetic circuitries 14b to 14d. Here, the sampling rate for sampling, conducted on an output signal, is the same as the sampling rate for sampling that is conducted on the reference waveform.

After the arithmetic circuitries 14b to 14d receive the sampling data, they first determine whether the sampling data includes a peak. For example, the arithmetic circuitries 14b to 14d determine whether any of the values of the sampling data "$x_1$" to "$x_{11}$" exceeds a predetermined threshold "a", as illustrated in FIG. 6B. Here, if none of the values of the sampling data "$x_1$" to "$x_{11}$" exceeds the threshold "a", the arithmetic circuitries 14b to 14d do not perform the operation using the above-described chi-squared test.

Conversely, if any of the values of the sampling data "$x_1$" to "$x_{11}$" exceeds the threshold "a", the arithmetic circuitries 14b to 14d determine the peak position of the sampling data "$x_1$" to "$x_{11}$". For example, the arithmetic circuitries 14b to 14d determine that the position where the difference value between the adjacent sets of sampling data intersects with zero is the peak position. If an explanation is given by using an example, the arithmetic circuitries 14b to 14d determine that the position where the value of the sampling data "$x_i - x_{i-1}$" is changed from plus to minus is the peak position. That is, the arithmetic circuitries 14b to 14d search for the point where there is a transition from an increase to a decrease in the output value of the sampling data, thereby extracting the peak position.

For example, the arithmetic circuitries 14b to 14d sequentially calculate each difference value of "$x_2-x_1$", "$x_3-x_2$", "$x_4-x_3$", and "$x_5-x_4$", and they determine that there is a peak at the position of "$x_5-x_4$", where the difference value is changed to minus. Then, the arithmetic circuitries 14b to 14d conduct the chi-squared test with Equation (1) that uses the sampling data and the comparison data, thereby calculating the chi-squared value "$X^2$". Here, the range for calculation of "$X^2$" may be arbitrarily set. For example, there may be a case where "$X^2$" is calculated by using all the sampling data, or there may be a case where several sets of sampling data, including the peak, are used.

Furthermore, the range for calculation of "$X^2$" may be changed in accordance with the shape of the reference waveform. For example, as illustrated in FIG. 5, in a case where the sharp peak is obtained, "$X^2$" may be calculated by using three points, including the peak. Here, if the data points to be used are increased, the accuracy with which the energy is estimated may be improved; however, there is a case where, if the subsequent X-ray is absorbed in the meantime, pile-up occurs, and the energy estimation accuracy is decreased. As described above, there is a trade-off relationship between the energy resolution and the pile-up, and therefore there may be a case where the data points to be used are determined depending on an application.

As described above, after the peak position is extracted, the arithmetic circuitries 14b to 14d use the stored comparison data and the sampling data to calculate the chi-squared value "$X^2$". For example, as illustrated in FIG. 7, the arithmetic circuitries 14b to 14d use four points, including the peak point "$x_4$", among the sampling data "$x_1$" to "$x_{11}$" to calculate "$X^2$". Specifically, the arithmetic circuitry 14b uses four points, including the peak point "$x_4$", in the sampling data and four points, including the peak point, in the comparison data on "15 keV" to calculate "$X^2$", and outputs it to the comparator 14e. In the same manner, the arithmetic circuitry 14c uses four points, including the peak point "$x_4$", in the sampling data and four points, including the peak point, in the comparison data on "30 keV" to calculate "$X^2$", and outputs it to the comparator 14e. Furthermore, the arithmetic circuitry 14d uses four points, including the peak point "$x_4$", in the sampling data and four points, including the peak point, in the comparison data on "45 keV" to calculate "$X^2$", and outputs it to the comparator 14e.

The comparator 14e compares "$X^2$", received from each of the arithmetic circuitries 14b to 14d, and outputs an electric signal to the counter that corresponds to the energy band of "$X^2$" that indicates the minimum value. For example, the comparator 14e outputs an electric signal to the counter 14g that corresponds to "30 keV".

Figure 8:
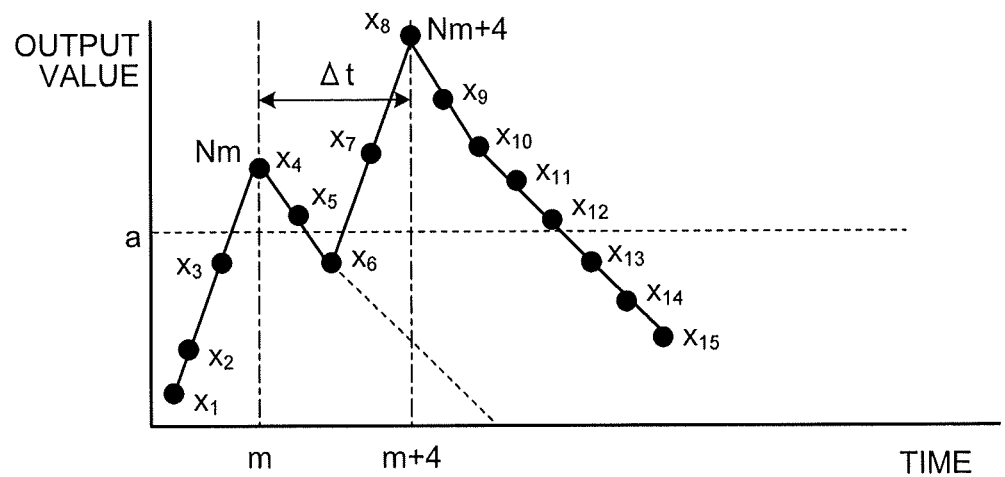
FIG. 8 is a diagram that illustrates an example of an operation at the time of pile-up by the data acquisition circuitry according to the first embodiment.

As described above, the data acquisition circuitry 14 uses the reference waveform of the signal, output from the detector 13, to estimate the energy of the X-ray photon that enters the detector 13. Here, the data acquisition circuitry 14 according to the first embodiment may also use the reference waveform to correct pile-up. FIG. 8 is a diagram that illustrates an example of an operation at the time of pile-up by the data acquisition circuitry 14 according to the first embodiment. For example, as illustrated in FIG. 8, if the X-ray is absorbed at the time "m−3", the pulse of "Nm" is detected at the time "m", and the pulse of "Nm+4" is detected at the time "m+4", the estimated output of the pulse at the time "m+4" is higher than in reality due to the effect of the pulse at the time "m".

Therefore, the data acquisition circuitry 14 corrects pile-up by the following operation that uses the reference waveform. First, the arithmetic circuitries 14b to 14d in the data acquisition circuitry 14 determine whether the sampling data, received from the ADC 14a, is affected by pile-up. Specifically, the arithmetic circuitries 14b to 14d perform the operation on the sampling data to determine the above-described peak position, thereby extracting the peak position from the sampling data. For example, the arithmetic circuitries 14b to 14d extract the sampling data "$x_4$" and "$x_8$" in FIG. 8, thereby calculating the time interval "$\Delta t$" between the peaks.

Here, the arithmetic circuitries 14b to 14d determine whether the calculated time interval "$\Delta t$" is shorter than the data length of the reference waveform so as to determine whether the sampling data is affected by pile-up. Specifically, if the time interval "$\Delta t$" between the peaks (pulses) is shorter than the data length of the reference waveform, the arithmetic circuitries 14b to 14d determine that the sampling data is affected by pile-up. Conversely, if the time interval "$\Delta t$" between the peaks (pulses) is longer than the data length of the reference waveform, the arithmetic circuitries 14b to 14d determine that the sampling data is not affected by pile-up. Here, the data length of the reference waveform corresponds to the number of sets of data that is sampled from the reference waveform, and it is for example "25" in the case of FIG. 5. That is, the arithmetic circuitries 14b to 14d determine whether the time interval "$\Delta t$" is shorter than the time of 25 points in the reference waveform.

For example, if the arithmetic circuitries 14b to 14d determine that "$\Delta t$", illustrated in FIG. 8, is longer than the data length of the reference waveform, it does not correct the pulse of "Nm+4". Conversely, if it is determined that "$\Delta t$", illustrated in FIG. 8, is shorter than the data length of the reference waveform, the arithmetic circuitries 14b to 14d conduct correction on the basis of the following Equation (2). Here, in Equation (2), "$X^2$" denotes the chi-squared value, "$x_i$" denotes the waveform (output value) based on the X-ray, transmitted through the subject, "$template_i$" denotes the reference waveform, and "$\sigma i$" denotes data error. Furthermore, in Equation (1), "N" denotes the constant by which the vertical axis of the reference waveform is multiplied.

$$X^2 = \sum_{i=j}^{k} \frac{(x_i - N \times template_i - N_m \times template_{i+\Delta t})^2}{\sigma_i^2} \quad (2)$$

Specifically, as represented in Equation (2), when the data "$x_i$" on the pulse for estimating the energy is compared with the comparison data "N×$template_i$", the arithmetic circuitries 14b to 14d conduct correction by using the output value of the pulse that is previous to the above pulse. For example, if the energy is estimated with regard to the pulse "Nm+4" by using the sampling data "$x_7$", "$x_8$", "$x_9$", and "$x_{10}$", the arithmetic circuitries 14b to 14d conduct subtraction on the output value of the pulse "Nm", which is previous to the pulse that corresponds to the times of "$x_7$", "$x_8$", "$x_9$", and "$x_{10}$", and then conduct a chi-squared test. For example, the arithmetic circuitries 14b to 14d subtract the output value of the pulse "Nm" at the time "m+4" from the value of the sampling data "$x_8$" and then uses it for a chi-squared test. In the same manner, the arithmetic circuitries 14b to 14d subtract the output value of the pulse "Nm" at the time of each sampling data from the value of the corresponding sampling data and then use it for a chi-squared test.

Here, the output value of the pulse "Nm" at the time of each sampling data may be calculated from the value of the reference waveform. That is, as the height of the waveform of the pulse "Nm" is already known from the estimation result of the energy of the pulse "Nm" and, furthermore, as the shape of the reference waveform is not changed, the output value after the elapse of "Δt" from the sampling data "$x_4$" may be derived from the output value of "$x_4$". As described above, to correct pile-up, the arithmetic circuitries 14b to 14d store the processing result of the comparator 14e with regard to at least the previous pulse. For example, the arithmetic circuitries 14b to 14d receive an output from the comparator 14e and store it. Furthermore, there may be a case where the pulse information, which is used for correction, is not only the previous pulse information but also the second or more previous pulse information. In such a case, the arithmetic circuitries 14b to 14d store the second or more previous pulse information.

Figure 9:
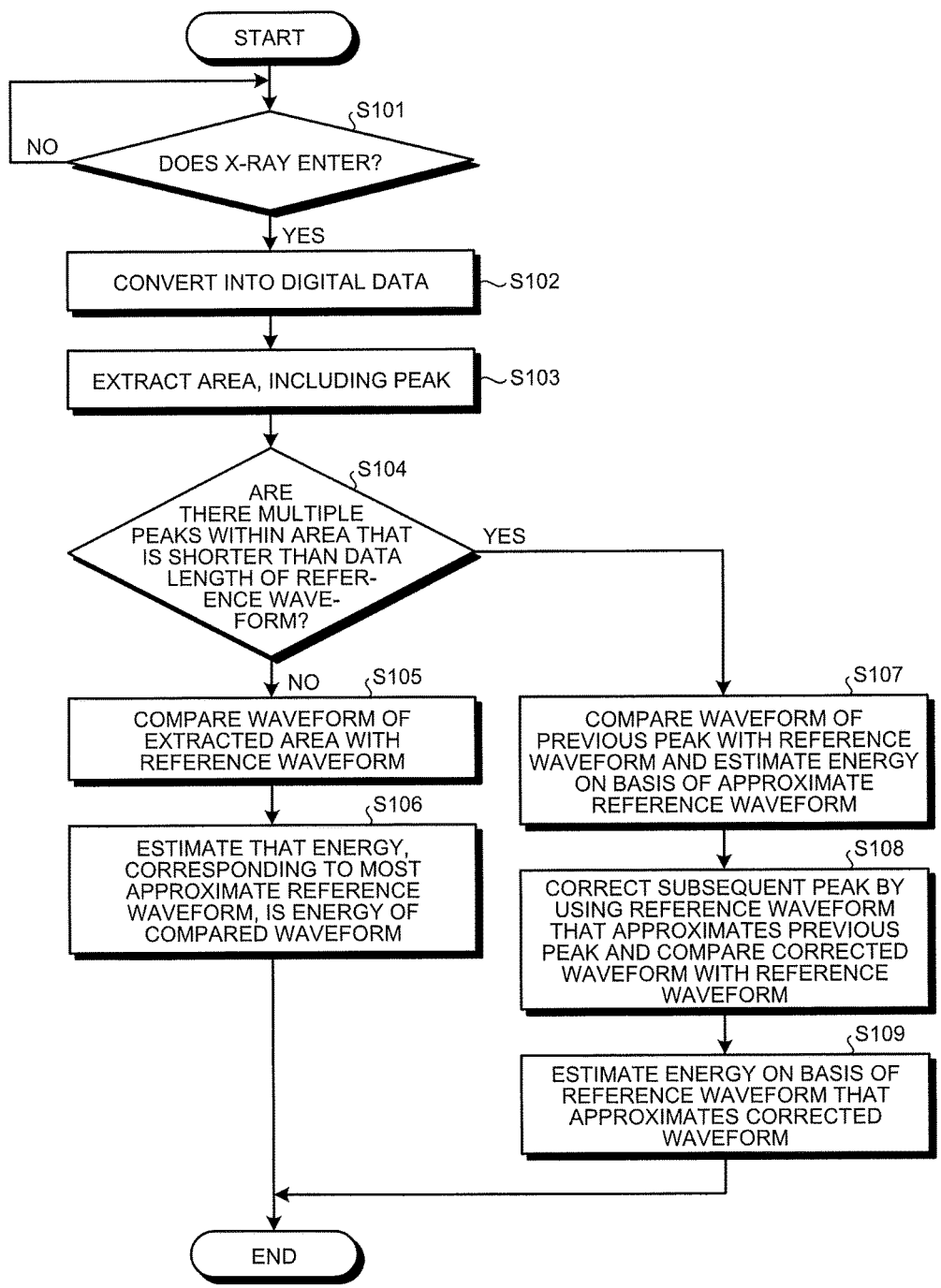
FIG. 9 is a flowchart that illustrates the steps of the operation of the photon-counting type X-ray CT apparatus according to the first embodiment.

Next, with reference to FIG. 9, an explanation is given of an operation of the photon-counting type X-ray CT apparatus 1 according to the first embodiment. FIG. 9 is a flowchart that illustrates the steps of the operation of the photon-counting type X-ray CT apparatus 1 according to the first embodiment. As illustrated in FIG. 9, if an X-ray enters the detection element 131 (Yes at Step S101), the ADC 14a converts the signal, received from the detection element 131, into digital data (sampling data) (Step S102).

Then, the arithmetic circuitries 14b to 14d extract the area, including the peak, from the sampling data that is received from the ADC 14a (Step S103) and determine whether there are multiple peaks within the time range that is shorter than the data length of the reference waveform (Step S104). Here, if it is determined that there are not multiple peaks within the time range that is shorter than the data length of the reference waveform (No at Step S104), the arithmetic circuitries 14b to 14d compare the waveform in the extracted area with the reference waveform (Step S105). Then, the comparator 14e estimates that the energy, corresponding to the most approximate reference waveform, is the energy of the compared waveform (Step S106).

Conversely, if it is determined that there are multiple peaks within the time range that is shorter than the data length of the reference waveform during the determination at Step S104 (Yes at Step S104), the arithmetic circuitries 14b to 14d compare the waveform of the previous peak with the reference waveform, and the comparator 14e estimates the energy on the basis of the approximate reference waveform (Step S107).

Then, the arithmetic circuitries 14b to 14d correct the subsequent peak by using the reference waveform that approximates the previous peak and compare the corrected waveform with the reference waveform (Step S108). Afterward, the comparator 14e estimates the compared energy on the basis of the reference waveform that approximates the corrected waveform (Step S109).

As described above, according to the first embodiment, the comparison function 141 compares the reference waveform of the signal, output from the detector 13 that detects radiation, with the waveform of the detection signal based on the radiation, which enters the detector 13 through the subject and which is detected by the detector 13. The estimation function 142 uses the comparison result by the comparison function 141 to estimate the information about the radiation that enters the detector 13 through the subject. Here, the comparison function 141 compares the waveform of the detection signal based on the X-ray, which is transmitted through the subject and enters the detector 13, with the reference waveform of each X-ray energy in the detector 13. The estimation function 142 estimates that the energy, corresponding to the reference waveform that approximates the waveform of the detection signal, is the energy of the X-ray, which is transmitted through the subject and enters the detector 13. Therefore, with the photon-counting type X-ray CT apparatus 1 according to the first embodiment, it is possible to improve the image quality, and it is possible to provide a photon-counting type X-ray CT apparatus with higher stability, to which an indirect-conversion type detector is applied.

Furthermore, according to the first embodiment, the comparison function 141 extracts a predetermined area, including the peak, from the waveform of the detection signal, and it compares the waveform in the extracted predetermined area with the waveform in the area, which corresponds to the predetermined area, of the reference waveform of each X-ray energy. The estimation function estimates that the energy, which corresponds to the reference waveform that approximates the waveform in the predetermined area, is the energy of the X-ray that is transmitted through the subject and enters the detector 13. Therefore, the photon-counting type X-ray CT apparatus 1 according to the first embodiment makes it possible to improve the processing speed for energy estimation.

Furthermore, according to the first embodiment, the comparison function 141 divides multiple peaks, included in the waveform of the detection signal, as each detection signal that is caused by the incidence of a single photon, uses the waveform that corresponds to the previous peak among the peaks to correct the subsequent peak, and compares the waveform of the predetermined area, including the previous peak, and the waveform of the predetermined area, including the corrected subsequent peak, with the reference waveform of each X-ray energy. The estimation function 142 uses each comparison result to estimate the energy of the photon, which corresponds to the previous peak, and the energy of the photon, which corresponds to the subsequent peak. Furthermore, the comparison function 141 determines that the reference waveform that approximates the waveform of the predetermined area, including the previous peak, is the waveform that corresponds to the previous peak, and it corrects the height of the subsequent peak by using the reference waveform that is determined to be the waveform that corresponds to the previous peak. Therefore, the photon-counting type X-ray CT apparatus 1 according to the first embodiment may reduce the effect of pile-up and may improve the image quality. Furthermore, the photon-counting type X-ray CT apparatus 1 according to the first embodiment may conduct correction on multiple pile-ups, thereby improving the image quality.

Furthermore, with the photon-counting type X-ray CT apparatus 1 according to the first embodiment, even if a scintillator with a low response speed is used in the indirect-conversion type detector, pile-up may be corrected. As described above, although indirect-conversion type detectors have a high X-ray absorption efficiency and a high stability compared to direct-conversion type detectors, they have a longer time constant and a low response speed, and therefore they are easily affected by pile-up. However, the photon-counting type X-ray CT apparatus 1 according to the first embodiment may correct pile-up as described above even if it uses the above indirect-conversion type detector.

Therefore, even if the photon-counting type X-ray CT apparatus 1 according to the first embodiment uses the scintillator, of which the conversion efficiency is high and the brightness is high although the time constant is long and the response speed is low, it may correct pile-up, thereby further improving the image quality.

Furthermore, according to the first embodiment, the comparison function 141 extracts the area of the waveform of the detection signal, where the value exceeds the predetermined threshold and it increases and decreases, as the predetermined area that includes the peak. Therefore, the photon-counting type X-ray CT apparatus 1 according to the first embodiment makes it possible to extract the area that includes the peak with high accuracy.

Second Embodiment

Figure 10:
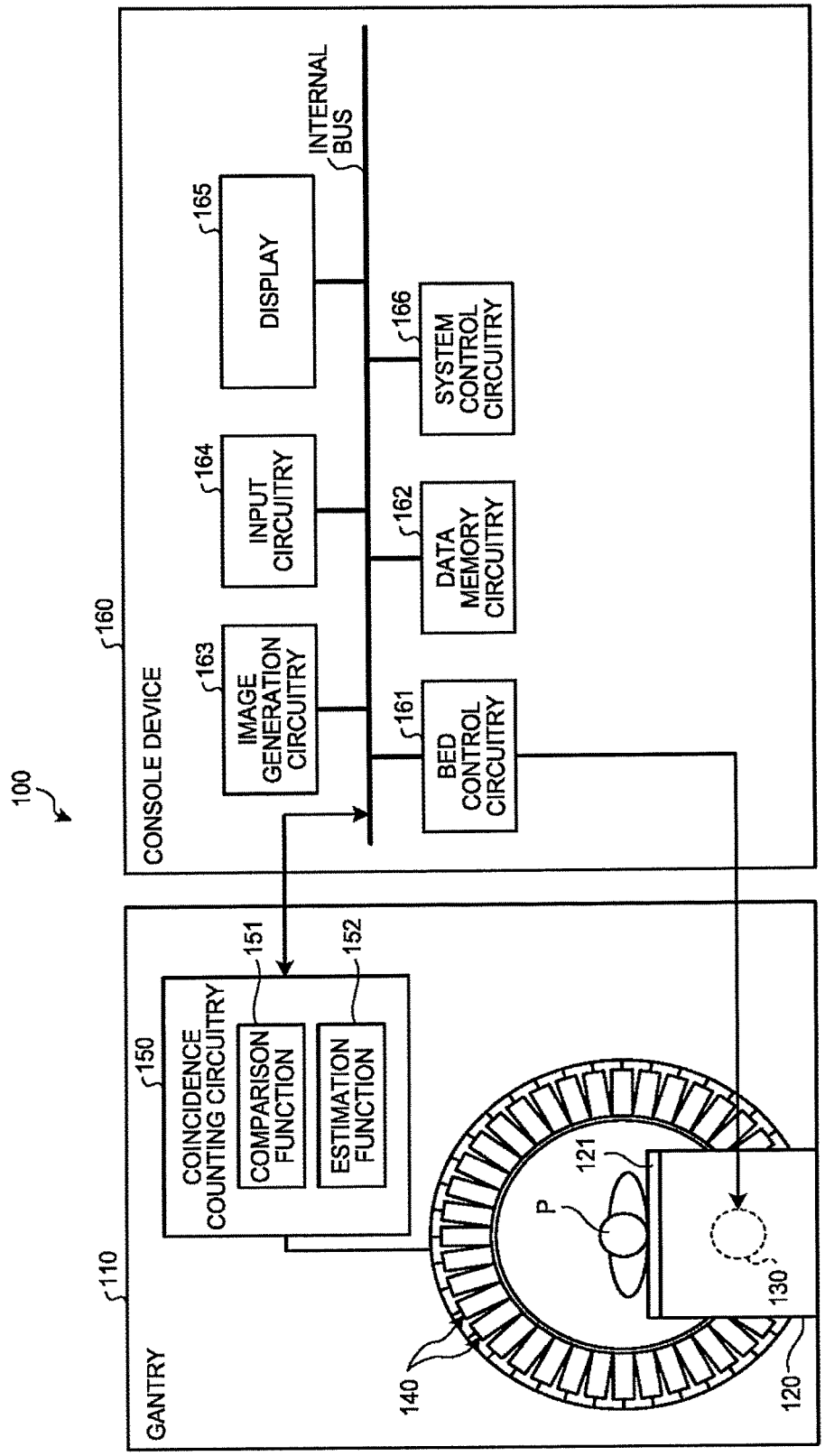
FIG. 10 is a diagram that illustrates an example of the configuration of a PET apparatus according to a second embodiment.

In the first embodiment, an explanation is given of an embodiment of the photon-counting type X-ray CT apparatus. Next, an embodiment of the PET apparatus is explained. FIG. 10 is a diagram that illustrates an example of the configuration of a PET apparatus 100 according to a second embodiment. As illustrated in FIG. 10, the PET apparatus 100 according to the second embodiment includes a gantry 110 and a console device 160.

The gantry 110 detects a pair of gamma rays, emitted from positive electrons, and collects the count information in accordance with the detection result. As illustrated in FIG. 10, the gantry 110 includes a top board 121, a bed 120, bed drive circuitry 130, a detector module 140, and coincidence counting circuitry 150. Furthermore, the gantry 110 has a hollow, which is an image taking hole, as illustrated in FIG. 10.

The top board 121 is a bed on which the subject P is laid, and it is provided on the bed 120. The bed drive circuitry 130 moves the bed 120 under the control of bed control circuitry 161 that is described later. For example, the bed drive circuitry 130 moves the bed 120 so as to move the subject P into the image capturing hole of the gantry 110.

The detector module 140 detects gamma rays, emitted from the subject P. As illustrated in FIG. 10, the detector modules 140 are provided such that they enclose the subject P in a ring shape in the gantry 110. Here, the detector module 140 is a photon-counting method Anger-type detector, and it includes for example a scintillator, a photomultiplier tube, and a light guide.

The coincidence counting circuitry 150 generates the coincidence counting information for determining the incident direction of a pair of gamma rays, emitted from positive electrons, on the basis of the output result from each of the detector modules 140. Specifically, the coincidence counting circuitry 150 calculates the position of the center of gravity on the basis of the energy of the incident gamma ray that corresponds to the position of the photomultiplier tube that converts the visible light, which is scattered and output by the scintillator, into an electric signal for output at the same timing and the intensity of the electric signal, thereby determining the incident position of the gamma ray (the position of the scintillator) in the detector module 140. Furthermore, the coincidence counting circuitry 150 integrates the intensity of the electric signal, output from each photomultiplier tube, thereby calculating the energy value of the gamma ray that enters the detector module 140.

Then, from the output results of the detector module 140, the coincidence counting circuitry 150 finds (coincidence finding) the combination of output results of which the incident timing (time) of the gamma ray falls within the time window width of a certain time period and the energy value falls within a certain energy window width. Furthermore, the coincidence counting circuitry 150 generates the coincidence counting information (coincidence list) where the found combination of output results is the information on the coincidence counting of two annihilation photons. Then, the coincidence counting circuitry 150 transmits the coincidence counting information as the gamma-ray projection data for PET image reconstruction to the console device 160 that is illustrated in FIG. 10. Here, the line that connects the two detection positions, where the two annihilation photons are coincidentally counted, is called Line of Response (LOR). Furthermore, there may be a case where the coincidence counting information is generated by the console device 160. Furthermore, as illustrated in FIG. 10, the coincidence counting circuitry 150 implements a comparison function 151 and an estimation function 152, and the details are given later.

The console device 160 receives operations of the PET apparatus 100 from an operator, controls capturing of PET images, and generates PET images by using the coincidence counting information that is acquired by the gantry 110. Specifically, as illustrated in FIG. 10, the console device 160 includes the bed control circuitry 161, data memory circuitry 162, image generation circuitry 163, input circuitry 164, a display 165, and system control circuitry 166. Furthermore, each component, included in the console device 160, is connected via an internal bus.

The input circuitry 164 is a mouse, a keyboard, or the like, which is used to input various commands or various settings by an operator of the PET apparatus 100, and it transfers the input various commands or various settings to the system control circuitry 166. The display 165 is a monitor, or the like, which is viewed by the operator, and under the control of the system control circuitry 166, it displays PET images or displays a graphical user interface (GUI) for receiving various commands or various settings from the operator. The bed control circuitry 161 controls the bed drive circuitry 130.

The data memory circuitry 162 stores various types of data that is used by the PET apparatus 100. The image generation circuitry 163 uses, for example, a successive approximation technique to reconstruct a PET image from the coincidence counting information (projection data), generated by the coincidence counting circuitry 150. Then, the image generation circuitry 163 stores the reconstructed PET image in image data 52 in the data memory circuitry 162. The system control circuitry 166 controls operations of the gantry 110 and the console device 160, thereby performing the overall control on the PET apparatus 100. Specifically, the system control circuitry 166 controls the bed control circuitry 161 so as to control PET scan that is conducted by the gantry 110. Furthermore, the system control circuitry 166 controls the image generation circuitry 163 so as to control image reconstruction processing or image generation processing of the console device 160. Furthermore, the system control circuitry 166 controls various types of image data, stored in the data memory circuitry 162, to be presented on the display 165.

Heretofore, the overall configuration of the PET apparatus 100 according to the second embodiment is explained. Here, each processing function, performed by each of the above-described circuitry, is stored in the data memory circuitry 162 in the form of a program executable by the computer. Furthermore, each circuitry reads and executes each program from the data memory circuitry 162, thereby implementing the above-described various functions. For example, the comparison function 151 and the estimation function 152, which are the components of the coincidence counting circuitry 150, are stored in the data memory circuitry 162 in the form of a program executable by the computer. The coincidence counting circuitry 150 is processor that reads and executes each program from the data memory circuitry 162, thereby implementing the function that corresponds to each program. In other words, in a state where each of the programs has been read, the coincidence counting circuitry 150 has each of the functions that are illustrated in FIG. 10. Here, the comparison function 151, explained in the present embodiment, is equivalent to a comparing unit that is described in a claim. Furthermore, the estimation function 152 is equivalent to an estimating unit that is described in a claim. Moreover, the word "processor", used in the above explanation, is the same as that described in the first embodiment.

With the above-described configuration, the PET apparatus 100 according to the second embodiment improves the image quality due to the operation of the coincidence counting circuitry 150, which is explained below in detail. Specifically, the coincidence counting circuitry 150 uses the reference waveform of the signal, output from the detector module 140, to estimate the arrival time of gamma rays, thereby improving the image quality.

For example, the comparison function 151 of the coincidence counting circuitry 150 compares the waveform of the detection signal based on the gamma ray, which enters the detector module 140 from inside the subject, with the reference waveform at each time, which is obtained by moving the reference waveform on the temporal axis. The estimation function 152 estimates that the time in the reference waveform that approximates the waveform of the detection signal is the arrival time of the gamma ray. Here, the estimation function 152 estimates that the time when the value of the cross-correlation function of the waveform of the detection signal and the reference waveform is maximum is the arrival time of the gamma ray.

Figure 11:
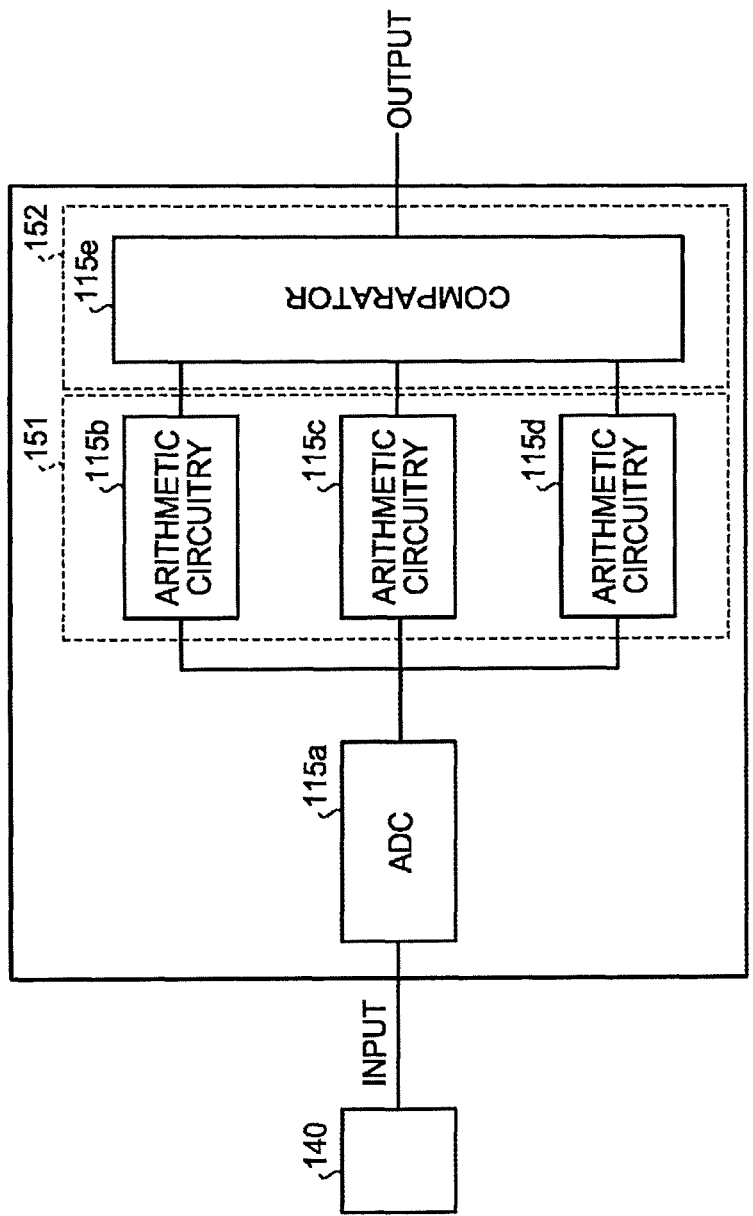
FIG. 11 is a diagram that illustrates an example of the configuration of coincidence counting circuitry according to the second embodiment.

An explanation is given below of an example of the configuration for implementing the above-described coincidence counting circuitry 150. FIG. 11 is a diagram that illustrates an example of the configuration of the coincidence counting circuitry 150 according to the second embodiment. As illustrated in FIG. 11, the coincidence counting circuitry 150 according to the second embodiment includes an ADC 115a, arithmetic circuitries 115b to 115d, and a comparator 115e, and each of them is provided at the subsequent stage of the scintillator of the detector module 140. Here, in FIG. 11, the arithmetic circuitries 115b to 115d are equivalent to the above-described comparison function 151, and the comparator 115e is equivalent to the above-described estimation function 152.

The ADC 115a converts a pulse signal, output from the detector module 140, into a digital signal. For example, the ADC 115a samples the input pulse signal at a predetermined sampling rate (e.g., 250 Msps). Then, the ADC 115a outputs the sampling data to each of the arithmetic circuitries 115b to 115d.

The arithmetic circuitries 115b to 115d compare the sampling data, output from the ADC 115a, with the reference waveform of the output signal in the detector module 140. Here, the arithmetic circuitries 115b to 115d according to the second embodiment use the cross-correlation function (cross correlation), represented by the following Equation (3), to compare the sampling data with the reference waveform. Here, in Equation (3), "CC" denotes the cross-correlation function, "x" denotes the waveform (output value) based on the gamma ray that is emitted from the subject, and "template" denotes the reference waveform.

$$CC(\Gamma) = \sum_{t=m}^{n} x(t) \text{ template } (t + \Gamma) \quad (3)$$

Figure 12:
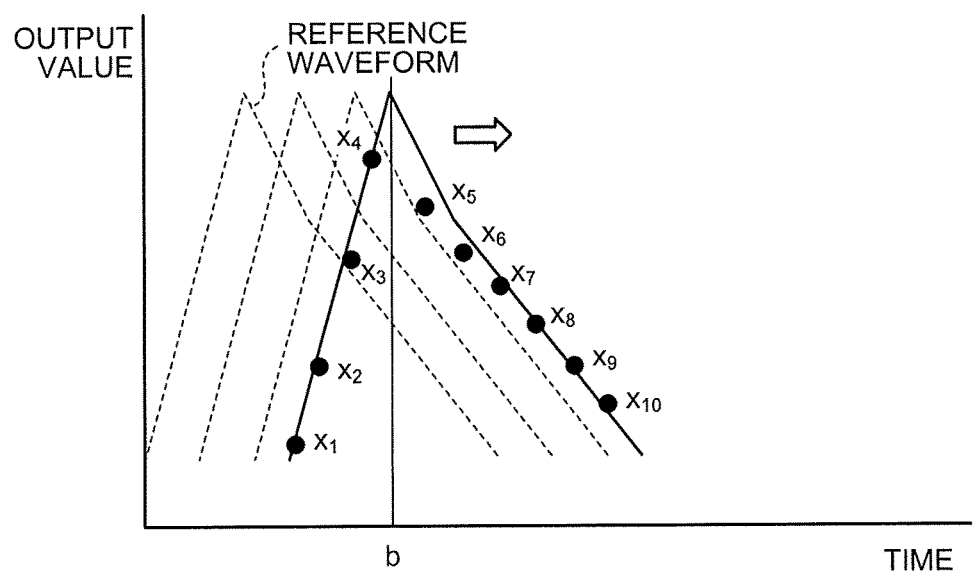
FIG. 12 is a diagram that illustrates an example of processing by the coincidence counting circuitry according to the second embodiment.

Specifically, as represented in Equation (3), the coincidence counting circuitry 150 evaluates the product of the sampling data and the data on the reference waveform, thereby estimating the arrival time of the gamma ray. FIG. 12 is a diagram that illustrates an example of processing by the coincidence counting circuitry 150 according to the second embodiment. For example, as illustrated in FIG. 12, the coincidence counting circuitry 150 calculates the CC with the sampling data while moving the reference waveform on the temporal axis. Here, "CC" is maximum at the time when the reference waveform and the sampling data approximate most; therefore, the coincidence counting circuitry 150 calculates "CC" while shifting the reference waveform by a predetermined time "τ", and it estimates that the time "b", where "CC" is maximum, is the arrival time of the gamma ray. As the sampling data is the digital data that is acquired at a predetermined sampling rate, if the peak is extracted by using only the sampling data, there is a possibility that the peak is not properly extracted. However, by using the peak at the time when the sampling data most approximates the reference waveform, the arrival time of the gamma ray may be determined with a high accuracy.

Here, according to the second embodiment, too, the comparison data "template (t+τ)", where the reference waveform is moved by a predetermined time, may be previously calculated and stored in each of the arithmetic circuitries 115b to 115d. For example, each of the arithmetic circuitries 115b to 115d stores the comparison data at a different time, calculates the cross-correlation function "CC" by using the sampling data, received from the ADC 115a, and the comparison data, and outputs it to the comparator 115e. The comparator 115e outputs the time in the comparison data, which is used to calculate "CC" that indicates the largest value among the received three "CC", as the arrival time of the gamma ray that corresponds to the sampling data.

Furthermore, for estimation of the arrival time of the gamma ray by using the above-described cross-correlation function, the ADC with a high sampling rate is used to acquire the sampling data from the reference waveform. Thus, the peak position in the reference waveform may be accurately determined. Furthermore, even if the sampling rate is low for sampling on the signal of the gamma ray that is emitted from the subject, the arrival time of the gamma ray may be accurately determined by using the sampling data from the above-described reference waveform.

Furthermore, in the above-described embodiment, an explanation is given of a case where, for example, all the sampling data, acquired by the ADC 115a, is used; however, this is not a limitation on the embodiment, and as described in the first embodiment, there may be a case where the peak position is extracted and several sets of sampling data, including the peak position, is used. In such a case, the comparison function 151 extracts a predetermined area, including the peak, of the waveform of the detection signal, and it compares the waveform in the extracted predetermined area with the waveform in the area, which corresponds to the predetermined area, of the reference waveform. The estimation function 152 estimates that the time in the reference waveform that approximates the waveform in the predetermined area is the arrival time of the gamma ray.

Figure 13A:
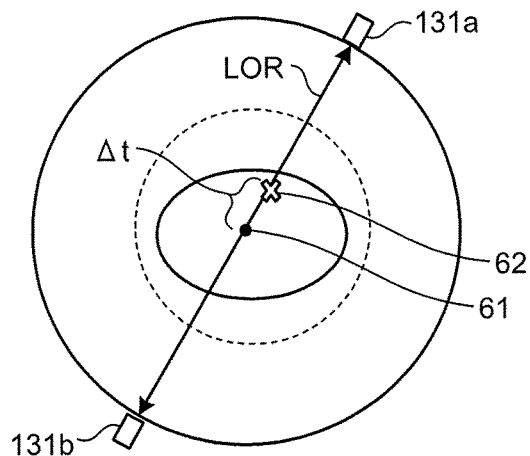
FIG. 13A is a diagram that illustrates an example of the TOF by a PET apparatus according to the second embodiment.
Figure 13B:
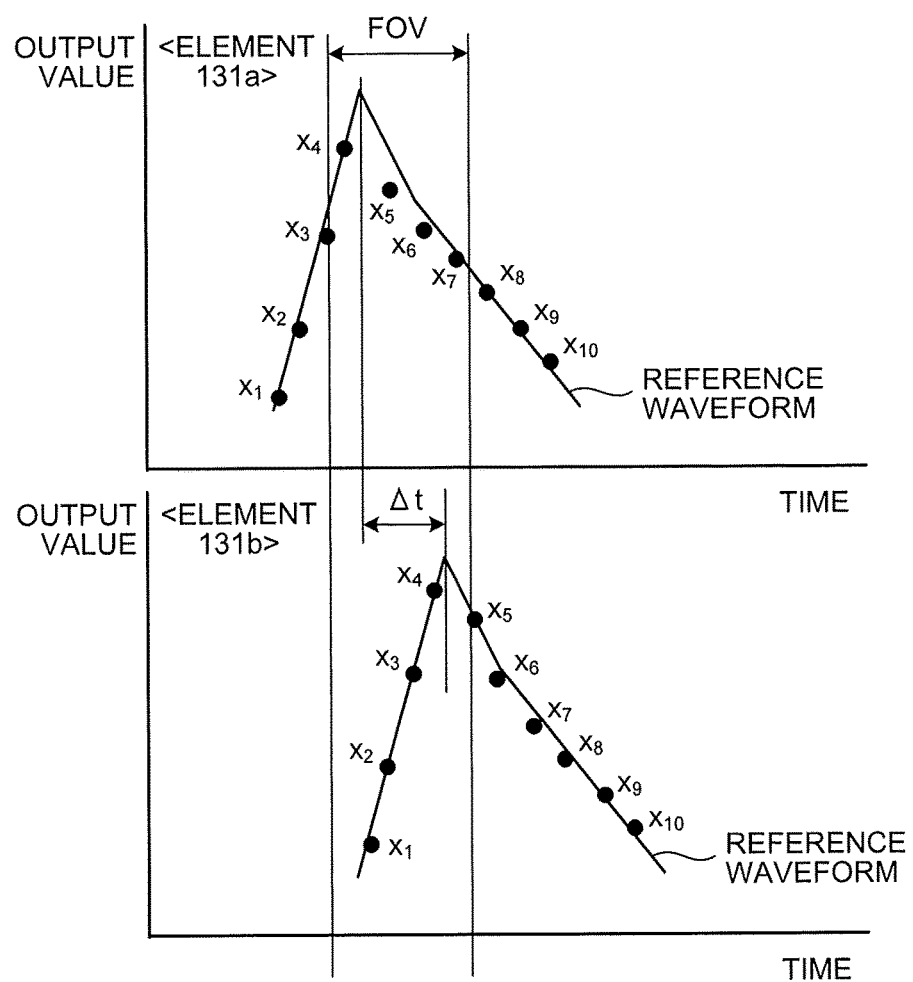
FIG. 13B is a diagram that illustrates an example of the TOF by the PET apparatus according to the second embodiment.

As described above, the coincidence counting circuitry 150 estimates the arrival time of the gamma ray by using the cross-correlation function that uses the reference waveform, thereby determining the arrival time with high accuracy. As a result, coincidence counting may be accurately performed, and the accuracy of Time-of-Flight (TOF) may be improved. FIGS. 13A and 13B are diagrams that illustrate an example of the TOF by the PET apparatus 100 according to the second embodiment. For example, as illustrated in FIG. 13A, after a detection element 131a and a detection element 131b detect gamma rays, the coincidence counting circuitry 150 determines the arrival time of each gamma ray during the operation that uses the above-described cross-correlation function.

Furthermore, as illustrated in FIG. 13B, the coincidence counting circuitry 150 determines that the combination of output results, of which the arrival time, determined in accordance with the reference waveform, falls within the time window width based on the FOV of the PET apparatus 100 and of which the energy value falls within a certain energy window width, is the information on the pair annihilation gamma-ray. Here, as illustrated in FIG. 13B, the coincidence counting circuitry 150 calculates the difference "Δt" in the arrival time of the pair annihilation gamma ray and conducts TOF on the basis of the calculated "Δt". Specifically, as illustrated in FIG. 13A, the coincidence counting circuitry 150 determines that a position 62, which is moved by the distance of "Δt" from a middle point 61 of the LOR, connecting the detection element 131a and the detection element 131b, is a position where the pair annihilation gamma ray occurs. In this way, with the PET apparatus 100 according to the second embodiment, the arrival time of the gamma ray may be determined with high accuracy and, as a result, the accuracy of the TOF may be improved.

Next, with reference to FIG. 14, an explanation is given of an operation of the PET apparatus 100 according to the second embodiment. FIG. 14 is a flowchart that illustrates the steps of the operation performed by the PET apparatus 100 according to the second embodiment. As illustrated in FIG. 14, after a gamma ray enters the detection element (Yes at Step S201), the ADC 115a converts the signal, received from the detection element, into digital data (sampling data) (Step S202).

Afterward, the arithmetic circuitries 115b to 115d calculate the cross-correlation function of the sampling data (detected waveform), received from the ADC 115a, and the reference waveform (Step S203). Then, the comparator 115e estimates that the time when the cross-correlation function is maximum is the arrival time of the gamma ray (Step S204). Then, the coincidence counting circuitry 150 generates the coincidence counting information on the basis of the estimated arrival time of the gamma ray (Step S205).

As described above, according to the second embodiment, the comparison function 151 compares the waveform of the detection signal based on the gamma ray, which enters the detector module 140 from inside the subject, with the reference waveform at each time, which is obtained by moving the reference waveform on the temporal axis. The estimation function 152 estimates that the time in the reference waveform, which approximates the waveform of the detection signal, is the arrival time of the gamma ray. Furthermore, the estimation function 152 estimates that the time when the value of the cross-correlation function of the waveform of the detection signal and the reference waveform is maximum is the arrival time of the gamma ray. Therefore, with the PET apparatus 100 according to the second embodiment, determination of the arrival time of the gamma ray and the TOF may be accurately conducted, and the image quality may be improved.

Third Embodiment

Although the first and second embodiments are explained above, various different embodiments may be implemented other than the above-described first and second embodiments.

For example, an explanation is given of a case where the indirect-conversion type detector, which uses the scintillator and the optical sensor, is used as a detector according to the above-described embodiment. However, this is not a limitation on the embodiment, and there may be a case where a direct-conversion type detector, which uses a semiconductor, is used. In such a case, for example, it is possible to appropriately use the one in which the shape of the waveform of an output signal, output from the detector, does not depend on the energy. For example, if silicon is used as the material of the semiconductor, the waveform of an output signal is often constant, and therefore it is applicable to the above-described embodiment. Furthermore, even in a case where CdTe, CdZnTe, GaAs, or the like, is used as the material of the semiconductor, if the detector allows incidence of X-rays by using the edge-on geometry where the thickness of the detector is reduced, it is applicable to the above-described embodiment.

Figure 15:
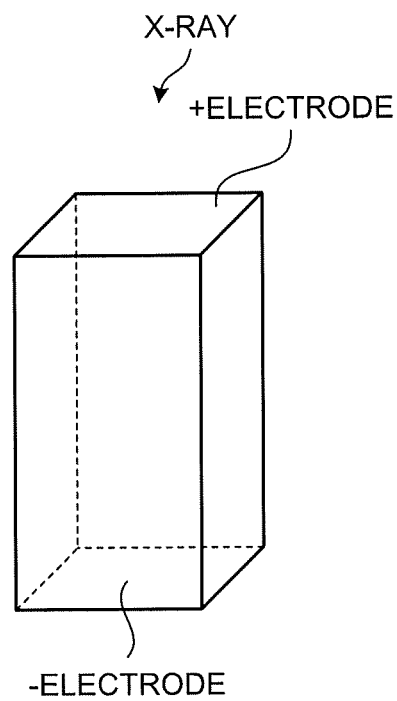
FIG. 15 is a diagram that illustrates an example of the geometry of a detector according to a third embodiment.
Figure 16:
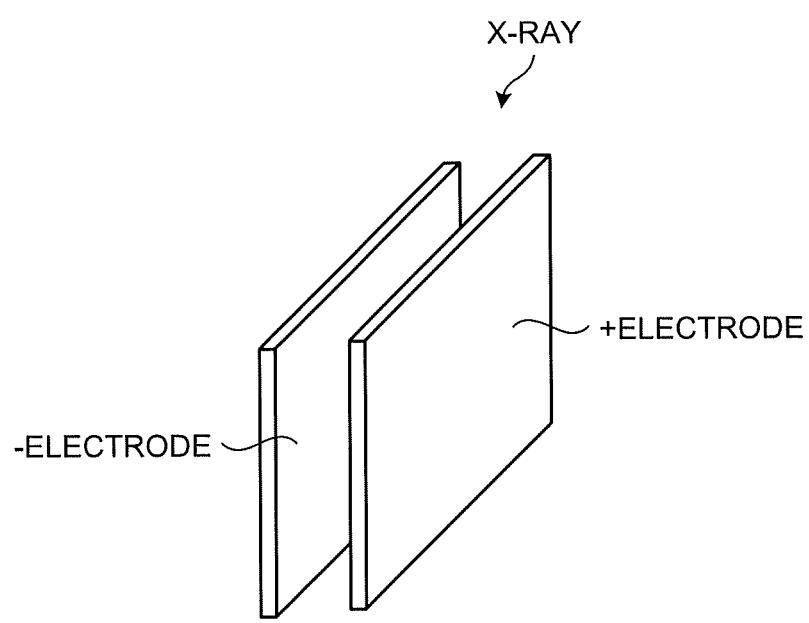
FIG. 16 is a diagram that illustrates an example of the geometry of a detector according to the third embodiment.

An explanation is given below of a typical direct-conversion type detector and an edge-on detector with reference to FIGS. 15 and 16. FIGS. 15 and 16 are diagrams that illustrate an example of the geometry of the detector according to a third embodiment. Here, FIG. 15 illustrates the typical detector. Furthermore, FIG. 16 illustrates the edge-on detector.

The direct-conversion type detector outputs signals when electrons and holes, which are generated when the detection element absorbs X-rays, move toward the positive electrode and the negative electrode. As illustrated in FIG. 15, the detection element in the typical detector has geometry such that any one of the electrodes is provided on the side where X-rays are incident. Here, electrons and holes, generated when X-rays are absorbed, have different mobility within the detection element, that is, the speed of electrons is high, and the speed of holes is low. Therefore, in the case of the typical geometry, illustrated in FIG. 15, the waveform of the output signal is different depending on the position of the detection element, at which the incident X-ray is absorbed.

For example, if an X-ray is absorbed on the positive electrode side of the detection element, electrons with high mobility instantaneously move to the positive electrode so that a signal indicating a sharp rise is output, and holes with low mobility slowly move to the negative electrode so that a signal indicating a moderate rise is output. Conversely, if an X-ray is absorbed on the negative electrode side of the detection element, it takes time for even electrons with high mobility to reach the positive electrode, and holes with low mobility slowly move to the negative electrode, whereby a signal indicating a moderate rise is output. As described above, in the direct-conversion type detector that has the typical geometry, the shape of the waveform is changed in accordance with the position where an X-ray is absorbed, and therefore it is difficult to apply it to the above-described embodiment.

However, in the case of the detector that has the edge-on geometry, illustrated in FIG. 16, the difference in the mobility of electrons and holes has hardly any effect, and the waveform of the output signal is the same. Specifically, in the case of the edge-on geometry, as illustrated in FIG. 16, the positive electrode and the negative electrode are arranged parallel in the direction perpendicular to the incident direction of X-rays, and the detection element, interposed therebetween, is configured to be thin; therefore, a configuration is such that, regardless of the position in the detection element where an X-ray is absorbed, the difference in the mobility of electrons and holes has hardly any effect. Therefore, in the case of the detector that has the edge-on geometry, illustrated in FIG. 16, the waveform of the output signal is hardly changed, and therefore it is applicable to the above-described embodiment. Furthermore, in the case of silicon, as compared to the other materials, the moving speeds of electrons and holes are high, and the difference in the mobility of electrons and holes has a small effect on the waveform. Therefore, if silicon is used as the material of the detection element, even the detector that has the typical geometry is applicable to the above-described embodiment.

Furthermore, according to the above-described embodiment, the reference waveform of each X-ray energy, which is used for comparison with the waveform of the detection signal (output signal), may be optionally set in accordance with various conditions. For example, the data acquisition circuitry 14 according to the present embodiment may use the reference waveform that corresponds to the energy near the k-absorption edge of the contrast agent in a case where the reference waveform is compared with the waveform of the output signal based on the X-ray that is transmitted through the subject, to which the contrast agent is given, and that enters the detector 13. Specifically, the data acquisition circuitry 14 compares the waveform of the detection signal based on the X-ray, which is transmitted through the subject to which the contrast agent is given and which enters the detector 13, with the reference waveform of each X-ray energy near the k-absorption edge of the contrast agent, and it acquires the detection signal that has the waveform that approximates the reference waveform that corresponds to the energy of the X-ray in the vicinity of the k-absorption edge.

Specifically, "N", which corresponds to the value of the energy of the X-ray near the k-absorption edge of the contrast agent, is calculated by using the relation equation of the X-ray energy and "N", and it is stored in the arithmetic circuitries 14b to 14d of the data acquisition circuitry 14. In other words, the arithmetic circuitries 14b to 14d store the comparison data "N×template$_i$" that uses "N", corresponding to the energy of the X-ray near the k-absorption edge of the contrast agent, calculates the chi-squared value "X$^e$" of the sampling data, output from the ADC 14a, and the comparison data, and outputs it to the comparator 14e.

Here, there are various types of contrast agents to be given to the subject, and the k-absorption edge is different depending on the used substance. For example, barium (Ba), iodine (I), gadolinium (Gd), or the like, are known as the contrast agent, and the k-absorption edge is different depending on each substance. Therefore, the arithmetic circuitries 14b to 14d store the comparison data "N×template$_i$" that corresponds to the given contrast agent, calculates the chi-squared value "X$^2$" of the sampling data, output from the ADC 14a, and the comparison data, and outputs it to the comparator 14e. Here, it is illustrated that the data acquisition circuitry 14 is provided with only the three circuitry, i.e., the arithmetic circuitries 14b to 14d; however, the data acquisition circuitry 14 may include any number of arithmetic circuitry in accordance with the number of sets of comparison data stored. An explanation is given below of a case where, for example, gadolinium is used as the contrast agent.

Figure 17A:
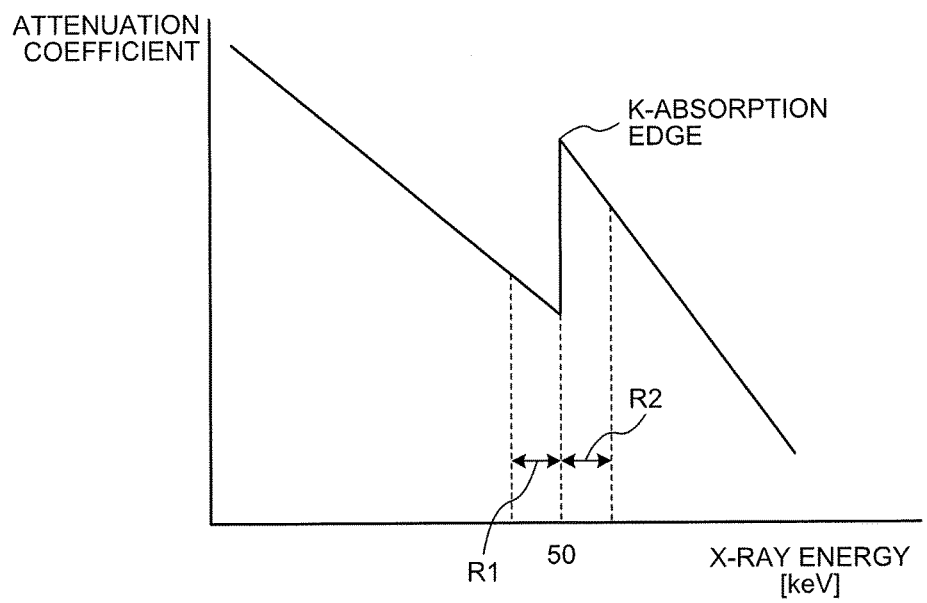
FIG. 17A is a diagram that illustrates an example of processing by data acquisition circuitry according to the third embodiment.
Figure 17B:
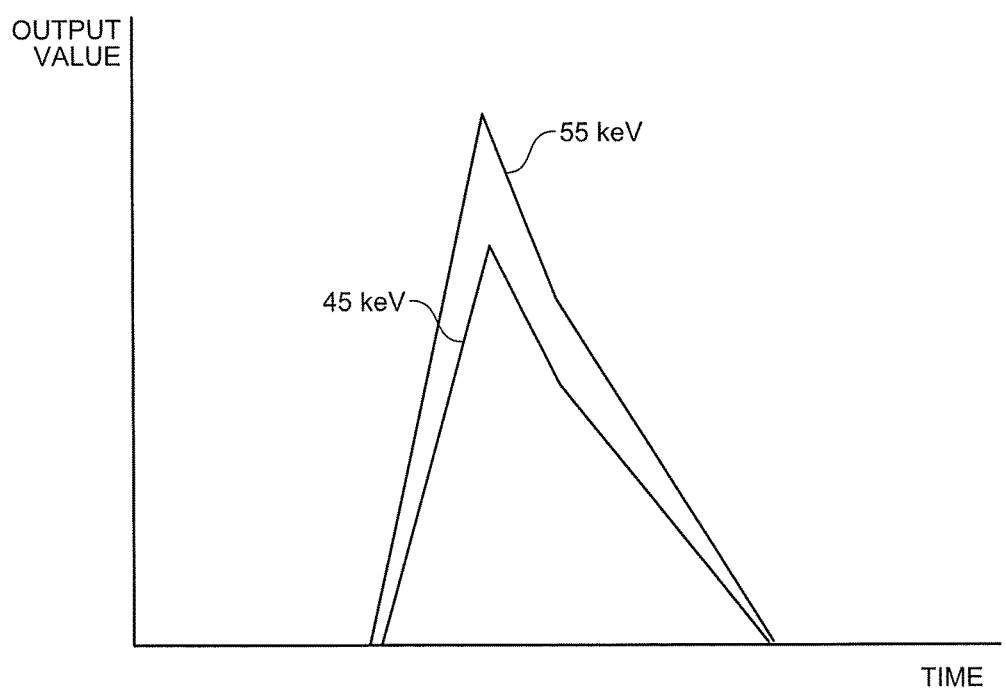
FIG. 17B is a diagram that illustrates an example of processing by data acquisition circuitry according to the third embodiment.

FIGS. 17A and 17B are diagrams that illustrate an example of processing by the data acquisition circuitry according to the third embodiment. FIG. 17A illustrates the k-absorption edge of gadolinium, and FIG. 17B illustrates an example of the reference waveform that is used if the contrast agent is gadolinium. Furthermore, in FIG. 17A, the vertical axis indicates the attenuation coefficient, and the horizontal axis indicates the X-ray energy (keV). Furthermore, in FIG. 17B, the vertical axis indicates the output value, and the horizontal axis indicates the time.

As illustrated in FIG. 17A, the k-absorption edge of gadolinium is about "50 keV", and absorption of X-rays is large at about "50 keV". That is, with regard to gadolinium, absorption of X-rays is significantly changed in the vicinity of about "50 keV". Therefore, if gadolinium is used as the contrast agent, images with different contrast effects may be generated at the energy band in the vicinity of about "50 keV" as a boundary. For example, at the energy band (e.g., an area R1 that is illustrated in FIG. 17A) before the k-absorption edge, as absorption of X-rays is small, images with a low contrast effect are generated. Conversely, at the energy band (e.g., an area R2 that is illustrated in FIG. 17A) after the k-absorption edge, as absorption of X-rays is large, images with a high contrast effect are generated.

Therefore, for example, as illustrated in FIG. 17B, the data acquisition circuitry 14 uses the reference waveforms of "45 keV" and "55 keV", which are the average values in the X-ray energy bands "40 to 50 keV" and "50 to 60 keV", respectively, in the vicinity of about "50 keV", which is the k-absorption edge of gadolinium, to discriminate the sampling data that corresponds to the X-ray energy band in the vicinity of the k-absorption edge of gadolinium. For example, two arithmetic circuitries out of the arithmetic circuitries 14b to 14d store the comparison data "N×template$_i$", which uses "N" that corresponds to "45 keV", and the comparison data "N×template$_i$", which uses "N" that corresponds to "55 keV", respectively. Furthermore, the two arithmetic circuitries out of the arithmetic circuitries 14b to 14d calculate the chi-squared value "X$^2$" of the sampling data, output from the ADC 14a, and the comparison data, and outputs it to the comparator 14e.

The comparator 14e compares the two chi-squared values "X$^2$", output from the two arithmetic circuitries out of the arithmetic circuitries 14b to 14d, and it outputs an electric signal to the counter that corresponds to the energy band of the chi-squared value "X$^2$" that indicates the smallest value. For example, two counters out of the counters 14f to 14h correspond to "40 to 50 keV" and "50 to 60 keV", respectively.

The photon-counting type X-ray CT apparatus 1 uses the count data on the energy bands, which are discriminated as above, to generate the CT image of "40 to 50 keV" and the CT image of "50 to 60 keV". For example, the photon-counting type X-ray CT apparatus 1 conducts subtraction on the generated CT image of "40 to 50 keV" and the CT image of "50 to 60 keV" so as to generate a CT image with a higher contrast effect.

In the above-described embodiment, an explanation is given of a case where the comparison data is changed on the basis of the k-absorption edge of the contrast agent. Next, an explanation is given of a case where the comparison data is changed in accordance with the degree of beam hardening. That is, an explanation is given of a case where "N" in the comparison data "N×template$_i$" is changed in accordance with the degree of beam hardening of the X-ray, transmitted through the subject. Specifically, the data acquisition circuitry 14 changes the energy of the X-ray, which corresponds to the reference waveform to be compared with the waveform of the detection signal based on the X-ray, in accordance with the degree of beam hardening of the X-ray, which is transmitted through the subject and enters the detector 13. If the degree of beam hardening of the X-ray, transmitted through the subject, is high, e.g., in a case where the body thickness of the subject is thick, or in a case where the site with bones densely packed is captured, the energy band to be discriminated may be set in detail on the side of a higher energy band.

Figure 18:
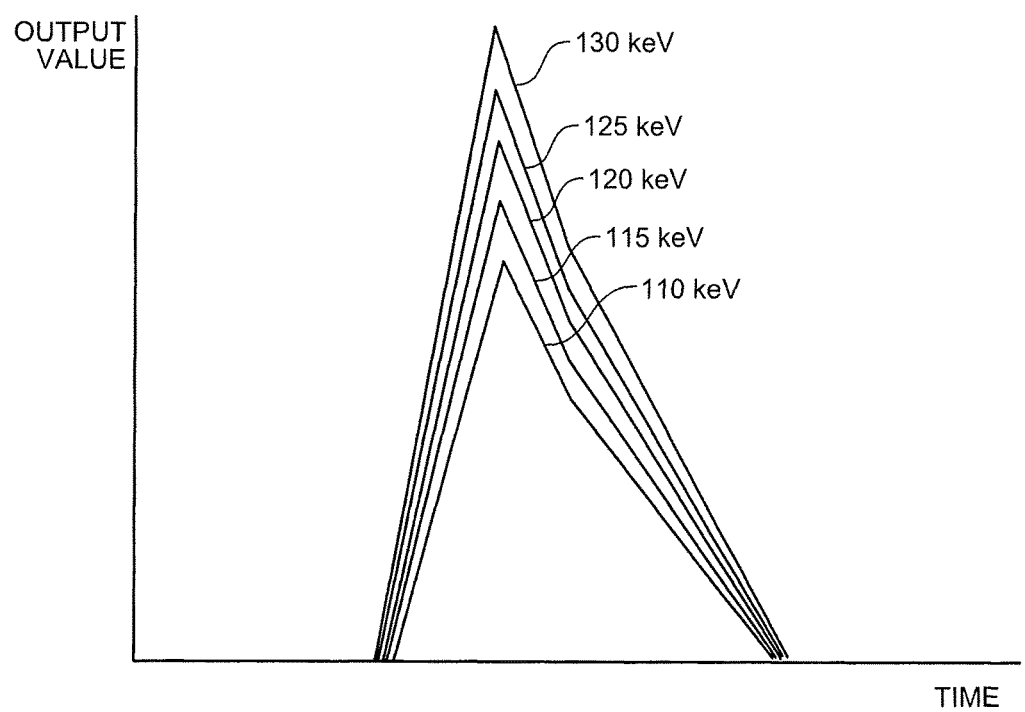
FIG. 18 is a diagram that illustrates an example of the reference waveform according to the third embodiment.

FIG. 18 is a diagram that illustrates an example of the reference waveform according to the third embodiment. In FIG. 18, the vertical axis indicates the output value, and the horizontal axis indicates the time. For example, as illustrated in FIG. 18, the data acquisition circuitry 14 uses the reference waveforms of "110 keV", "115 keV", "120 keV", "125 keV", and "130 keV" to discriminate the sampling data that corresponds to each X-ray energy band. In this way, to discriminate the X-ray that is hardened due to beam hardening, the data acquisition circuitry 14 may set the energy band for discrimination in detail on the side of a higher energy band. Specifically, the data acquisition circuitry 14 calculates "N", which corresponds to "110 keV", "115 keV", "120 keV", "125 keV", and "130 keV", from the relation equation of the energy of the X-ray and "N", and it stores them in the arithmetic circuitry. In other words, the arithmetic circuitry stores the comparison data "N×template," that uses "N", which corresponds to "110 keV", "115 keV", "120 keV", "125 keV", and "130 keV", calculates the chi-squared value "$X^2$" of the sampling data, output from the ADC 14*a*, and the comparison data, and outputs it to the comparator 14*e*. Here, if the comparison data on "110 keV", "115 keV", "120 keV", "125 keV", and "130 keV" is stored, the data acquisition circuitry 14 includes five arithmetic circuitries.

As described above, by changing the X-ray energy of the comparison data in accordance with the degree of beam hardening, it is possible to conduct energy discrimination in accordance with the radiation quality of the X-ray, transmitted through the subject. Furthermore, the arithmetic circuitry, included in the data acquisition circuitry 14, may be effectively used. For example, in the data acquisition circuitry that includes three arithmetic circuitries, if the degree of beam hardening is high, the three arithmetic circuitries are assigned to energy bands on the side of high energy band, and if the degree of beam hardening is low, the three arithmetic circuitries are assigned to energy bands that cover a wide energy. Thus, without increasing the arithmetic circuitry, energy discrimination may be conducted in accordance with the radiation quality of the X-ray, transmitted through the subject.

Furthermore, components of each device, illustrated in the first embodiment, are functionally conceptual and do not necessarily need to be physically configured as illustrated in the drawings. Specifically, specific forms of separation and combination of each device are not limited to those depicted in the drawings, and a configuration may be such that all or some of them are functionally or physically separated or combined in an arbitrary unit depending on various types of loads, usage, or the like. Furthermore, all or any of various processing functions performed by each device may be implemented by a CPU and a program that is analyzed and executed by the CPU, or it may be implemented as wired logic hardware.

Furthermore, the data acquisition method, described in the first embodiment, may be performed if a prepared data acquisition program is performed by a computer, such as a personal computer or workstation. The data acquisition program may be distributed via a network, such as the Internet. Furthermore, the data acquisition program may be recorded in a recording medium readable by a computer, such as a hard disk, flexible disk (FD), CD-ROM, MO, or DVD, and may be executed when it is read from the recording medium by the computer.

As described above, according to each of the embodiments, the image quality may be improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A data acquisition device comprising
processing circuitry configured to
compare a reference waveform with a waveform of a detection signal, the waveform of the detection signal being generated by detecting radiation, the reference waveform having a peak value that changes to correspond to an energy of the radiation and having a shape approximating a signal that, is output from a detector that detects the detection signal, and the radiation entering the detector through a subject and being detected by the detector, and
estimate information about the radiation, which enters the detector through the subject, in accordance with a comparison result between the waveform of the detection signal and the reference waveform for which the peak value approximates a peak value of the waveform of the detection signal.

2. The data acquisition device according to claim 1, wherein the processing circuitry is configured to
compare a reference waveform of each X-ray energy in the detector with the waveform of the detection signal, wherein the waveform of the detection signal is generated by detecting an X-ray, which is transmitted through the subject and which enters the detector, and
estimate that the energy of the radiation, which is detected to generate the waveform of the detection signal is an energy of the reference waveform that approximates the waveform of the detection signal.

3. The data acquisition device according to claim 2, wherein the processing circuitry is configured to
compare, within a predetermined area including a peak of the waveform of the detection signal, the waveform of the detection signal with the reference waveform of each X-ray energy, and
estimate that the energy corresponding to the reference waveform that approximates the waveform of the detection signal within the predetermined area is the energy of the detected X-ray generating the waveform of the detection signal.

4. The data acquisition device according to claim 3, wherein the processing circuitry is configured to
identify respective peaks within the waveform of the detection signal as each being caused by detecting respective X-rays, use a waveform that corresponds to a previous peak among the peaks to correct a subsequent peak, and compare, within an area including a first predetermined area that includes the previous peak and a second predetermined area that includes the corrected subsequent peak, the waveform of the detection signal with a reference waveform of each X-ray energy, and estimate an energy of an X-ray corresponding to the previous peak, and estimate an energy of an X-ray corresponding to the subsequent peak.

5. The data acquisition device according to claim 4, wherein the processing circuitry is configured to determine a first reference waveform that approximates the waveform of the detection signal within the first predetermined area is a waveform that corresponds to the previous peak and use the first reference waveform to correct a height of the subsequent peak.

6. The data acquisition device according to claim 3, wherein the processing circuitry is configured to determine an area of the waveform of the detection signal in which a value of the waveform of the detection signal exceeds a predetermined threshold as the predetermined area that includes the peak.

7. The data acquisition device according to claim 1, wherein the processing circuitry is configured to compare the reference waveform at respective time delays with the waveform of the detection signal, wherein the waveform of the detection signal is generated by detecting a gamma ray, the reference waveform at respective time delays is obtained by moving the reference waveform on a temporal axis, and estimate that a time delay for which in the reference waveform at respective time delays approximates the waveform of the detection signal corresponds to an arrival time of the gamma ray.

8. The data acquisition device according to claim 7, wherein the processing circuitry is configured to estimate that a time when a value of a cross-correlation function of the waveform of the detection signal and the reference waveform is maximum is an arrival time of the gamma ray.

9. The data acquisition device according to claim 7, wherein the processing circuitry is configured to compare, within a predetermined area including a peak of the waveform of the detection signal, the waveform of the detection signal with the reference waveform at respective time delays, and estimate that a time delay for which the reference waveform at respective time delays approximates the waveform of the predetermined area is an arrival time of the gamma ray.

10. The data acquisition device according to claim 2, wherein the processing circuitry is configured to compare the waveform of the detection signal with the reference waveform of each X-ray energy near a k-absorption edge of a contrast agent, and acquire a detection signal that has a waveform that approximates the reference waveform that corresponds to an energy of an X-ray in vicinity of the k-absorption edge.

11. The data acquisition device according to claim 2, wherein the processing circuitry is configured to change the energy of the X-ray, which corresponds to the reference waveform to be compared with the waveform of the detection signal, in accordance with a degree of beam hardening of the X-ray, which is transmitted through the subject and enters the detector.

12. An X-ray CT apparatus comprising:

a detector configured to detect an X-ray that is transmitted through a subject and generate a detection signal; and processing circuitry is configured to compare a waveform of the detection signal with a reference waveform of each X-ray energy in the detector, determine an amplitude of the reference waveform for which a peak value of the reference waveform approximates a peak value of the waveform of the detection signal, and estimate that an energy corresponding to the reference waveform having the determined amplitude, is an energy of the X-ray generating the detection signal.

13. A nuclear medicine diagnostic apparatus comprising:

a detector configured to detect a gamma ray that is emitted from inside a subject and generate a detection signal; and processing circuitry is configured to compare a waveform of the detection signal with a reference waveform at respective time delays, which is obtained by moving the reference waveform on a temporal axis, determine a time delay of the reference waveform for which the reference waveform approximates the waveform of the detection signal, and estimate that the determined time delay corresponds to an arrival time of the gamma ray.

* * * * *